US010730856B2

(12) United States Patent
Peters et al.

(10) Patent No.: US 10,730,856 B2
(45) Date of Patent: *Aug. 4, 2020

(54) BENZIMIDAZOLE DERIVATIVES AS EP4 LIGANDS

(71) Applicant: BAYER PHARMA AKTIENGESELLSCHAFT, Berlin (DE)

(72) Inventors: Olaf Peters, Tabarz (DE); Nico Bräuer, Falkensee (DE); Ulrich Bothe, Berlin (DE); Marcus Koppitz, Berlin (DE); Jens Nagel, Daxweiler (DE); Gernot Langer, Falkensee (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/105,832

(22) PCT Filed: Dec. 16, 2014

(86) PCT No.: PCT/EP2014/077955
§ 371 (c)(1),
(2) Date: Jun. 17, 2016

(87) PCT Pub. No.: WO2015/091475
PCT Pub. Date: Jun. 25, 2015

(65) Prior Publication Data
US 2016/0318905 A1 Nov. 3, 2016

(30) Foreign Application Priority Data
Dec. 19, 2013 (EP) .................................... 13198448

(51) Int. Cl.
C07D 403/04 (2006.01)
A61K 45/06 (2006.01)

(52) U.S. Cl.
CPC ............ C07D 403/04 (2013.01); A61K 45/06 (2013.01)

(58) Field of Classification Search
CPC ............................ C07D 403/04; A61K 45/06
See application file for complete search history.

(56) References Cited

U.S. PATENT DOCUMENTS

2004/0122046 A1  6/2004 Elliott

FOREIGN PATENT DOCUMENTS

| EP | 1257280 B1 | 5/2005 |
| EP | 2172447 A1 | 4/2010 |
| WO | 2002032422 A2 | 4/2002 |
| WO | 2002032900 A3 | 4/2002 |
| WO | 2003/000254 A1 | 1/2003 |
| WO | 2003086371 A2 | 10/2003 |
| WO | 2004067524 A1 | 8/2004 |
| WO | 2005/021508 A1 | 3/2005 |
| WO | 2005102389 A2 | 3/2005 |
| WO | 2005/105733 A1 | 9/2005 |
| WO | 2007121578 A1 | 11/2007 |
| WO | 2008017164 A1 | 2/2008 |
| WO | 2008/107373 A1 | 9/2008 |
| WO | 2008104055 A1 | 9/2008 |
| WO | 2009020588 A1 | 2/2009 |
| WO | 2010/124097 A2 | 10/2010 |
| WO | 2011/102149 A1 | 8/2011 |
| WO | 2014/086739 A1 | 6/2014 |
| WO | 2015091475 | 2/2015 |

OTHER PUBLICATIONS

Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chs. 9-10 provided.*
Okumura et al. (Bioorganic & Medicinal Chemistry Letters, 27 (2017), p. 1186-1192).*
Moreira et al. (Current Medicinal Chemistry, 2005, 12, 23-49).*
Utako Yokoyama et al, The Prostanoid EP4 Receptor and Its Signaling Pathway, Pharmacological Reviews, Jul. 2013, vol. 65, No. 3, 1010-1052.
Sales and Jabbour, Cyclooxygenase enzymes and prostaglandins in pathology of the endometrium 2003, Reproduction 126, 559-567.
Kuwano et al., Cyclooxygenase 2 is a key enzyme for inflammatory ytokine-induced angiogenesis 2004, FASEB J. 18, 300-310.
Kamiyama et al. EP2, a receptor for PGE2, regulates tumor angiogenesis through direct effects on endothelial cell motility and survival 2006, Oncogene 25, 7019-7028.
Chang et al., Regulation of vascular endothelial cell growth factor expression in mouse mammary tumor cells by the EP2 subtype of the prostaglandin E2 receptor 2005, Prostaglandins & other Lipid Mediators 76 (2005) 48-58.
Smith et al., Cyclooxygenase enzyme expression and E series prostaglandin receptor signalling are enhanced in heavy menstruation 2007, Human Reproduction, vol. 22, No. 5 pp. 1450-1456.
Imir et al., Aromatase Expression in Uterine Leiomyomata Is Regulated Primarily by Proximal Promoters I.3/II 2007, J Clin Endocrinol Metab 92, 1979-1982.
Fulton et al., Targeting Prostaglandin E EP Receptors to Inhibit Metastasis 2006, Cancer Res; 66(20): 9794-7.
Hull et al., Prostaglandin EP receptors: Targets for treatment and prevention of colorectal cancer? 2004, Mol Cancer Ther;3(8):1031-9.

(Continued)

Primary Examiner — Robert H Havlin
(74) Attorney, Agent, or Firm — McBee Moore & Vanik IP, LLC

(57) ABSTRACT

The present invention relates to novel benzimidazole derivatives of the general formula (I), to processes for their preparation and to their use for preparing pharmaceutical compositions for the treatment of disorders and indications associated with the EP4 receptor.

9 Claims, No Drawings

(56) References Cited

OTHER PUBLICATIONS

Wang et al., Cyclooxygenase-2: A Potential Target in Breast Cancer 2004, Seminars in Oncology, vol. 31, No. 1, Suppl 3: pp. 64-73.
Minami et al., Prostaglandin E Receptor Type 4-associated Protein Interacts Directly with NF-kappaB1 and Attenuates Macrophage Activation 2008, J Biol Chem., Apr. 11; 283(15): 9692-703.
Hoshino et al., Involvement of Prostaglandin E2 in Production of Amyloid-beta-peptides Both in Vitro and in Vivo 2007, J Biol Chem.; 282(45): 32676-88.
Cimino et al., Therapeutic Targets in Prostaglandin E2 Signaling for Neurologic Disease 2008, Current Medicinal Chemistry, 1863-1869.
Palumbo et al., Time-dependent changes in the brain arachidonic acid cascade during cuprizone-induced demyelination and remyelination 2011, Prostaglandins, Leukotrienes and Essential Fatty Acids 85: 29-35.
Kihara et al., Targeted lipidomics reveals mPGES-1-PGE2 as a therapeutic target for multiple sclerosis 2009, Proc Natl Acad Sci U. S. A, 106, Nr. 51: 21807-21812.
Liu et al., Prostaglandin E2 mediates proliferation and chloride secretion in ADPKD cystic renal epithelia 2012, Am J Physiol Renal Physiol 303: F1425-F1434.
Zeihhofer, Prostanoids in nociception and pain 2007, Biochemical Pharmacology 73; 165-174.
Murase et al. Effect of prostanoid EP4 receptor antagonist, CJ-042,794, in rat models of pain and inflammation European Journal of Pharmacology 580 (2008) 116-121.
Serezani et al. Prostaglandin E2 Suppresses Bacterial Killing in Alveolar Macrophages by Inhibiting NADPH Oxidase Am Respir Cell Mol Biol vol. 37. pp. 562-570, 2007.
Sheibanie et al., The Proinflammatory Effect of Prostaglandin E2 in Experimental Inflammatory Bowel Disease Is Mediated through the IL-233 IL-17 Axis 2007, The Journal of Immunology, 178: 8138-8147.
Ballinger et al., Critical Role of Prostaglandin E2 Overproduction in Impaired Pulmonary Host Response following Bone Marrow Transplantation 2006, The Journal of Immunology, 177: 5499-5508.
Wang et al., Prostaglandin E2 Alters Human Orbital Fibroblast Shape Through a Mechanism Involving the Generation of Cyclic Adenosine Monophosphate 1995, J Clin Endocrinol Metab 80: 3553-3560.
Giudice L C; Endometriosis; N Engl J Med 2010; 362: 2389-98.
Chishima F et al: Increased expression of cyclooxygenase-2 in local lesions of Endometriosis Patients AJRI 2002 48:50-56.
Sales K J and Jabbour H N; Cyclooxygenase enzymes and prostaglandins in pathology of the endometrium Reproduction (2003) 126:559-567.
Stratton P and Berkley K J; Chronic pelvic pain and endometriosis: translational evidence of the relationship and implications Human Reproduction Update, vol. 17, No. 3 pp. 327-346, 2011.
Petraglia F et al; Reduced pelvic pain in women with endometriosis: efficacy of long-term dienogest treatment; Arch Gynecol Obstet, Jan. 2012; 285 (1): 167-73.

\* cited by examiner

BENZIMIDAZOLE DERIVATIVES AS EP4 LIGANDS

The present invention relates to novel ligands of the human prostanoid receptor subtype EP4 and their use for the treatment and/or prophylaxis of diseases, and their use as medicaments and pharmaceutical preparations that contain the novel benzimidazole-5-carboxylic acid derivatives.

The clinical picture of endometriosis has been comprehensively investigated and described, even though the pathogenic mechanisms are still not completely known. Characteristic of endometriosis is a persistent colonization of endometrial tissue outside the uterine cavity, which leads to typical endometriosis foci. These lesions can be detected in varying distribution and occurrence in the muscular region of the uterus (internal endometriosis, adenomyosis), at various points of the abdominal cavity, e.g. the ligaments, on the parietal peritoneum of the Douglas pouch (peritoneal endometriosis), the intestinal wall, on the ovary (""endometrioma"") or rectovaginally (rectovaginal, frequently also deeply infiltrating, endometriosis). The newly established tissue retains key features of the original tissue (uterus, endometrium). Endometriosis has an inflammatory character and often manifests itself by various forms of lower abdominal pain. It is assumed that 10-20% of women of reproductive age are affected by endometriosis. Core symptoms of endometriosis are chronic lower abdominal pain, dysmenorrhoea, dyspareunia, dysuria, bleeding disorders and infertility. The symptoms usually occur in combination.

It is presumed that endometrial tissue that reaches the peritoneal cavity by retrograde menstruation via the oviduct can settle in the peritoneal tissue and causes the lesions observed in endometriosis (Stratton & Berkley, Giudice 2010). These lesions cause progressive local inflammation in the course of the disease and are characterized by up-regulation of COX2 enzyme and increased prostaglandin synthesis (Chishima et al. 2002; Sales & Jabbour 2003).

The actions of the prostaglandins are mediated by specific G-protein-coupled receptors, which are located in the cell membrane. Of particular interest is prostaglandin E2 (PGE2), which achieves a diversity of cellular actions, by binding to functionally different receptor subtypes, namely EP1, EP2, EP3 and EP4.

The prostaglandin receptor subtype EP4 (PTGR4) is one of the 4 human receptors that are activated by endogenously formed prostaglandin E2 (PGE2). EP4 belongs to the family of membrane-bound G-protein coupled receptors (GPCR) and, via coupling to a heterotrimeric G protein (Gs), activates primarily the formation of the intracellular signal molecule cAMP by stimulation of membrane-bound adenylate cyclases (Yokoyama et al., 2013; The Prostanoid EP4 Receptor and Its Signaling Pathway; Utako Yokoyama, Kousaku Iwatsubo, Masanari Umemura, Takayuki Fujita and Yoshihiro Ishikawa; Pharmacological Reviews, July 2013, Vol. 65, No 3, 1010-1052; (http://pharmrev.aspetioumals.org/content/65/3/1010.long#title15)

The expression of the receptor was detected on peripheral nerve endings of nociceptors, on macrophages and neutrophils. For these cell types, great importance was demonstrated in connection with endometriosis. It is assumed that the local inflammation of the endometriotic lesions makes a significant contribution to the genesis of the pain symptoms observed (Stratton & Berkley 2010; Giudice 2010).

Current therapeutic approaches for the treatment of diagnosed endometriosis are very restricted.

Thus, endometriosis can be treated by surgical removal of the endometriotic lesions in a laparoscopic intervention. Here, endometrial foci are removed surgically using heat (electrocauterization) or by excision (extirpation). In addition, during the intervention any adhesions present can be resolved, endometrial cysts can be removed and, in the case of the desire for children, the permeability of the oviducts can be checked by means of chromopertubation. The relapse rate after such an intervention, however, is very high (25-30%). Hysterectomy, that is the complete removal of the uterus, exists in such particularly difficult cases as the final therapeutic option.

In the case of particularly severe diseases, sometimes only the removal of both ovaries and of oviducts (bilateral salpingo-oophorectomy, adnexectomy) affords a definitive treatment.

Menstrual pain and prolonged or increased bleeding, which originate from endometriosis in the uterine muscle (adenomyosis uteri), can also be treated successfully by a hysterectomy.

These interventions, however, lead to infertility and a premature menopause with the problems associated therewith, which is why the use must be weighed well against the disadvantages.

Besides invasive surgical interventions, a medicinal therapy can also be taken into consideration. This is frequently used in the case of a large-area, possibly not completely operable attack, but is also employed in the case of mild to moderate disease. In addition to mainly symptomatic pain therapy using non-steroidal anti-inflammatory drugs (NSAID), four substance groups come into consideration in principle for this:
(a) combined oral contraceptives (consisting of oestrogen and gestagen) (OCs)
(b) gestagens
(c) GnRH analogues (GnRH=gonadotropin-releasing hormone) and
(d) Danazol®

The combined oral contraceptives (a) regulate the course of the cycle and reduce the menstrual flow. Their effectiveness in endometriosis patients presumably follows from this. However, patient satisfaction with this form of treatment is low, which is presumably to be attributed to side-effects due to the influencing of the hormone balance and unsatisfactory pain control. In addition, new studies indicate that long-term use of the hormonal active substances appears to be associated with an increased rate of deeply infiltrating endometriosis, a particularly painful form of endometriosis.

The use of OCs in the treatment of endometriosis is also described in the patent literature. Thus, EP 1257280 discloses that micronized drospirenone is suitable for the treatment of endometriosis. It is described there in paragraph [0045] that compositions of drospirenone having a low content of oestrogen or else without any oestrogen are suitable, inter alia, for the treatment of endometriosis. This is explained from the gestagenic property of drospirenone. In EP1257280, amounts of 0.5 to 10 mg of drospirenone are described as effective. Nothing is disclosed in this specification about the length of treatment of endometriosis with drospirenone.

WO2008/107373 describes mineralocorticoid receptor antagonists for the production of a medicament for the treatment of endometriosis. In addition to the use of compounds having pure antimineralocorticoid action, compounds are also proposed there that moreover also show an effect on the progesterone receptor, on the oestrogen receptor, on the glucocorticoid receptor and/or on the androgen receptor. In particular, the compounds disclosed in WO2008/

107373, spironolactone and the drospirenone mentioned beforehand, also have a gestagenic action.

The compound eplerenone mentioned in WO2008/107373 shows, as a pure MR antagonist, a relatively weak in vitro potency. MR antagonists are preferred that in in vitro trans activation assays have an at least 10-fold lower ICso compared with eplerenone.

Gestagens (b) are likewise employed in endometriosis. The starting point here is, on the one hand, the suppression of the function of the ovaries and, on the other hand, the induction of the terminal differentiation of the endometrium, decidualization, which finally leads to tissue death.

The gestagens simulate a pregnancy in the body and thus create a changed hormonal situation. Ovulation no longer takes place and the endometrium atrophies. In general, the endometriosis symptoms then subside within from 6 to 8 weeks.

Depot MPA (medroxyprogesterone acetate) and Visanne© (Dienogest) are licensed for endometriosis treatment. A distinct analgesic action of Visanne© occurs only after several weeks of treatment (Petraglia et al. 2011). There is no evidence on the generally desired rapid pain alleviation. In the case of MPA, a reduction of the bone mass can already occur even after an administration period of 6 months on account of the anti-oestrogenic action of the compound. It should therefore in no case be administered over a longer period of time than 2 years. Under treatment with Visanne, an undesired influencing of the bleeding profile can occur as a side-effect of the gestagenic properties. (specialist info side-effects).

In addition to the hormone cycle, gestagens in general also influence the bleeding profile, with bleeding disorders as a frequent side-effect of gestagens. This also relates to substances that are active on other hormone receptors and simultaneously have a gestagenic activity, such as, for example, spironolactone. As a result of defective angiogenesis (neovascularization, a process that takes place cyclically in the endometrium) during the decidualization of the endometrium, the vessel walls become fragile and "breakthrough bleeding" occurs, which takes place independently of menstrual bleeding and is characteristic of chronic treatment with gestagens.

The gonadotrophin-releasing hormone analogues (GnRH) (c) currently represent the gold standard of the licensed therapeutics against all stages of endometriosis. GnRH analogues block the pituitary gland completely. The menstrual cycle no longer takes place. These substances thus temporarily artificially transpose the body of the woman into the menopause and the endometriosis tissue can therefore also no longer jointly bleed. The tissue becomes hypotrophic.

On account of the side-effect profile, this therapeutic approach, however, is likewise only suitable for short-term use (up to 6 months). Thus, GnRH agonists induce post-menopausal symptoms such as hot flushes (80-90%), sleep disorders (60-90%), vaginal dryness (30%), headaches (20-30%), mood changes (10%) and decrease in bone density with accompanying increased risk of osteoporosis.

Apart from the side-effects mentioned, after ending the treatment the normal cycle sets in again within 2 to 3 months. In over 60% of the women affected, the symptoms of endometriosis then also return, such that a renewed treatment cycle must be considered.

Due to the disadvantages mentioned, GnRH analogues have thus far not gained any wide use in the treatment of endometriosis, even though these have replaced the standard therapy established in the 1970s with Danazol®, a gestagenic androgen, due to the somewhat better side-effect profile.

Danazol® (d) was the first "classical" therapeutic of endometriosis and the gold standard until the 1970s. In the case of relatively long administration, Danazol®, similarly to the male sex hormone testosterone, leads to a masculinization of the woman. The effects known for androgens, such as acne, hyperandrogenism, hirsutism and (irreversible) voice pitch change occur as further side-effects (note specialist info).

Danazol®, like the GnRH agonists, acts on the pituitary gland, which is responsible for the production of hormones that stimulate the ovaries. The production of oestrogens in the ovaries is adjusted in this way.

There is therefore an urgent need for alternative preparations, which allow a non-invasive treatment of endometriosis and which do not have the disadvantages of the prior art. A suitable option would be the specific blockade of the functions of the human EP4 receptor using suitable modulators.

EP4 antagonists are known in this context, but have not yet been licensed as medicaments. However, EP4 receptor-antagonistic properties of various structural classes have been described, which differ significantly from the compounds according to the invention in that they do not have their carbazolyl benzimidazole structure. Thus, WO2005/0121508, WO2005102389 and WO2005/105733 (Pfizer), for example, describe N-benzylarylamides, N-benzylheteroarylamides and [(1H-benzimidazol-1-yl)phenylethyl] aryl- and [(1H-benzimidazol-1-yl)phenylethyl]peteroarylsulphonylcarbamates for use in the case of pain, inflammation, osteoarthritis and rheumatoid arthritis. Pfizer also describes, in WO2002032422, WO2002032900 and WO2003086371, structures that generically include benzimidazoles, but cannot be substituted in position 2 by a fused tricycle such as carbazole. Thiophene-N-benzylamides in WO2008017164 and WO2009020588, indole-N-benzylamides in WO2007121578 and N-{[(6,8-dihydro-7H-pyrrolo[3,4-g]quinolin-7-yl)-aryl]methyl}sulphonylamides in WO2008104055 are addressed for nearly the same indication spectrum by Merck-Frosst. WO2010019796 (Chemietek) generically claims very widely polysubstituted heterobicycles, with the typical units of the compounds according to the invention, carbazole and benzimidazole, not occurring in the very few examples, and tricyclic substituents such as carbazole also not being addressed generically. WO2004067524 (Pharmagene Laboratories) describes furan derivatives for the treatment of headache and migraine, in which derivatives the furan ring is connected linearly to two further aryl- or heteroaryl units, in each case having six ring atoms.

EP2172447 (Astellas Pharma) claims generically in a very broad manner compounds that can consist of two heterocycles connected directly to one another, of which one, however, must be substituted by an aminocarbonyl group and the amino group must be further substituted by a substituent that carries a carboxyl group or a carboxyl surrogate, for the indications renal insufficiency and diabetic nephropathy.

Compounds are also described that are not EP4 antagonists, but are structurally related to the compounds according to the invention. US2004/0122046 (Pfizer) addresses carbazoles, which are connected directly to a heterocycle via position 3, that can also be benzimidazole, as NPY receptor antagonists for the treatment of obesity. In contrast to the compounds according to the invention, the NH of the benzimidazole unit, however, is mandatorily unsubstituted and the two six-membered rings of the carbazole unit can carry no further substituents. WO03/000254 or EP1162196 (Japan Tobacco) generically claims in a broad manner heterobicycles, which can be connected directly to a heterocycle, as a therapeutic for hepatitis C. If the heterocycle is a benzimidazole, this, in contrast to the compounds according to the invention, must be compulsorily connected directly to a cycloalkyl or cycloalkenyl unit by a bond in position 1. Paratek describes substituted benzimidazoles as anti-infectives in WO2010/124097. However, the benzimidazole, unlike in the compounds according to the invention, compulsorily carries an alkyl group that is substituted terminally by a carboxylic acid or phosphonic acid or sulphonic acid function or its derivatives in position 4; furthermore, heterocycloalkyl, but not heteroaryl, is permitted as a direct cyclic substituent in position 2. Starting from the prior art described, there was therefore no cause to modify the structures of the prior art according to the invention to obtain structures that act antagonistically on the EP4 receptor.

It is an object of the present invention to prepare compounds available in vivo and thus effective and stable, which act as potent and selective EP4 receptor ligands with antagonistic effect, and which are therefore suitable for the treatment and/or prophylaxis of disorders such as, for example, endometriosis.

This object was achieved by the compounds of the general formula I

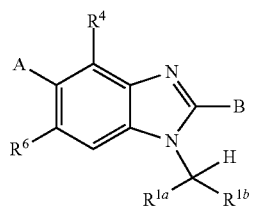

in which

A represents hydrogen, bromine, cyano, formyl, $C_1$-$C_3$-alkyl, 4- to 6-membered heterocyclyl, 5- to 6-membered heteroaryl, $R^{11}O$—$C(=O)$—$(CH_2)_p$—, $R^5R^{5'}N$—$C(=O)$—$(CH_2)_p$—, $R^{11}O$—$S(=O)_2$—$(CH_2)_p$—, $R^5R^{5'}N$—$S(=O)_2$—$(CH_2)_p$—, ($C_1$-$C_6$-alkyl)-$S(=O)_2$—, ($C_1$-$C_6$-alkyl)-$S(=O)(=NH)$— or ($C_3$-$C_6$-cycloalkyl)-$S(=O)(=NH)$—, where heteroaryl is preferably selected from the group consisting of pyrazolyl, imidazolyl, triazolyl, tetrazolyl, oxazolyl, isoxazolyl and oxadiazolyl, and where alkyl radicals may optionally be mono- or polysubstituted and where heterocyclyl radicals may optionally be mono- or polysubstituted by identical or different $C_1$-$C_3$-alkyl, trifluoromethyl or hydroxy substituents, and where heteroaryl radicals may optionally be mono- or polysubstituted by identical or different $C_1$-$C_3$-alkyl, trifluoromethyl or hydroxy substituents, B is selected from the following structures

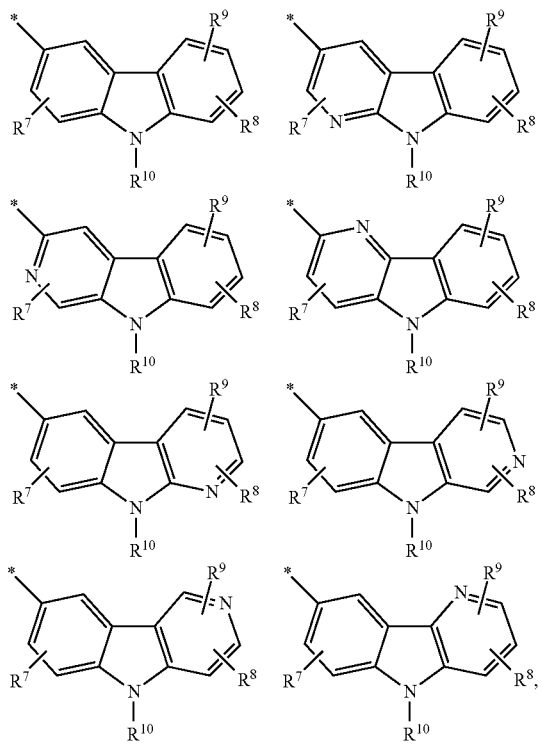

where * denotes the point of attachment in the molecule, $R^{1a}$, $R^{1b}$ independently of one another represent hydrogen, cyano, $C_1$-$C_5$-alkyl, $C_2$-$C_5$-alkenyl, $C_2$-$C_5$-alkynyl, ($C_3$-$C_6$-cycloalkyl)-$(CH_2)_m$—, (4- to 6-membered heterocyclyl)-$(CH_2)_n$—, ($C_1$-$C_5$-alkoxy)-($C_1$-$C_3$-alkyl)-, ($C_3$-$C_6$-cycloalkoxy)-($C_1$-$C_3$-alkyl)-, $H_2N$—($C_1$-$C_3$-alkyl)-, ($C_1$-$C_5$-alkyl)NH—($C_1$-$C_3$-alkyl)- or ($C_1$-$C_5$-alkyl)$_2$N—($C_1$-$C_3$-alkyl)-, where heterocyclyl is preferably selected from the group consisting of oxetanyl, tetrahydrofuranyl, tetrahydropyranyl, 1,4-dioxanyl, morpholinyl, azetidinyl, pyrrolidinyl, piperazinyl and piperidinyl, and where alkyl radicals, cycloalkyl radicals and heterocyclyl radicals may optionally be mono- or polysubstituted by identical or different halogen, $C_1$-$C_5$-alkyl, hydroxy, $C(=O)OH$, $HO$—$C(=O)$—($C_1$-$C_5$-alkyl)-, ($C_1$-$C_5$-alkyl)$O$—$C(=O)$—($C_1$-$C_5$-alkyl)- or ($C_1$-$C_5$-alkyl)-$S(=O)_2$— substituents, $R^4$ represents hydrogen, fluorine, chlorine, $C_1$-$C_2$-alkyl, $C_3$-$C_5$-cycloalkyl, $C_1$-$C_2$-alkoxy or ($C_3$-$C_4$-cycloalkyl)-$CH_2$—, where alkyl and cycloalkyl radicals may optionally by mono- or polysubstituted by identical or different halogen or hydroxy substituents, $R^5$, $R^{5'}$ independently of one another represent hydrogen, $C_1$-$C_7$-alkyl, ($C_1$-$C_7$-alkoxy)-($C_2$-$C_5$-alkyl)-, (4- to 6-membered heterocyclyl)-$(CH_2)_r$—, ($C_1$-$C_7$-alkyl)-$C(=O)$—, ($C_3$-$C_7$-cycloalkyl)-$C(=O)$—, phenyl-$(CH_2)_r$—$C(=O)$—, pyridyl-$(CH_2)_r$—$C(=O)$—, ($C_1$-$C_7$-alkyl)-$S(=O)_2$—, ($C_3$-$C_7$-cycloalkyl)-$S(=O)_2$—, phenyl-$(CH_2)_r$—$S(=O)_2$— or pyridyl-$(CH_2)_r$—$S(=O)_2$—, where heterocyclyl is preferably selected from the group consisting of oxetanyl, tetrahydrofuranyl, tetrahydropyranyl, 1,4-dioxanyl, morpholinyl, azetidinyl, pyrrolidinyl, piperazinyl and piperidinyl,
and
where $R^5$ and $R^{5'}$ independently of one another may be mono- or polysubstituted by identical or different halogen, hydroxy, $C_1$-$C_2$-alkyl, trifluoromethyl, ($C_1$-$C_5$-alkyl)NH—, ($C_1$-$C_5$-alkyl)$_2$N—, $C_1$-$C_2$-alkoxy or trifluoromethoxy,
or
$R^5$, $R^{5'}$ together with the nitrogen atom to which they are attached form a 4- to 6-membered heterocyclic ring which may optionally be mono- or polysubstituted by identical or different oxo, hydroxy, carboxy, $C_1$-$C_2$-alkyl or $C_1$-$C_2$-alkoxy substituents,
where a 6-membered heterocyclic ring may optionally contain, as further ring atom, a heteroatom selected from the group consisting of O and N,
$R^6$ represents hydrogen, fluorine, chlorine, methyl, trifluoromethyl, methoxy or trifluoromethoxy,
$R^7$ represents hydrogen, fluorine, chlorine, cyano, $SF_5$, $C_1$-$C_3$-alkyl, $C_3$—$O_5$-cycloalkyl,
$C_1$-$C_2$-alkoxy or ($C_3$-$C_4$-cycloalkyl)-$CH_2$—,
where alkyl and cycloalkyl radicals may optionally be mono- or polysubstituted by identical or different halogen radicals,
$R^8$ represents fluorine, chlorine, bromine, cyano, $SF_5$, $C_1$-$C_3$-alkyl, $C_3$-$C_5$-cycloalkyl, $C_1$-$C_2$-alkoxy or ($C_3$-$C_4$-cycloalkyl)-$CH_2$—,
where alkyl and cycloalkyl radicals may optionally be mono- or polysubstituted by identical or different halogen radicals,
$R^9$ represents fluorine, chlorine, bromine, cyano, $C_1$-$C_3$-alkyl or $C_1$-$C_2$-alkoxy,
where alkyl radicals may optionally be mono- or polysubstituted by identical or different halogen substituents, or
$R^9$ represents bromine and simultaneously $R^8$ represents hydrogen,
$R^{10}$ represents $C_1$-$C_5$-alkyl, $C_3$-$C_5$-alkenyl, $C_3$-$C_5$-alkynyl, ($C_3$-$C_6$-cycloalkyl)-$(CH_2)_n$—, (4- to 6-membered heterocyclyl)-$(CH_2)_n$— or ($C_1$-$C_7$-alkoxy)-($C_2$-$C_5$-alkyl)-,
where heterocyclyl is preferably selected from the group consisting of oxetanyl, tetrahydrofuranyl, tetrahydropyranyl, morpholinyl, pyrrolidinyl and piperidinyl,
and
where alkyl radicals, cycloalkyl radicals and heterocyclyl radicals may optionally be mono- or polysubstituted by identical or different halogen, $C_1$-$C_2$-alkyl, $C_1$-$C_2$-alkoxy or C(=O)OH radicals,
$R^{11}$ represents hydrogen, $C_1$-$C_7$-alkyl, $C_3$-$C_7$-cycloalkyl, phenyl-$(CH_2)_q$— or ($C_1$-$C_7$-alkoxy)-($C_2$-$C_5$-alkyl)-,
where phenyl may optionally be mono- or polysubstituted by identical or different $C_1$-$C_3$-alkyl, trifluoromethyl or hydroxy radicals,
m is 0, 1, 2 or 3,
n is 0, 1, 2 or 3,
p is 0, 1 or 2,
q is 1, 2 or 3 and
r is 0, 1, 2 or 3,
and diastereomers, enantiomers, solvates and salts or cyclodextrin clathrates thereof, for the preparation of medicaments.

Compounds according to the invention are the compounds of the formula (I) and the stereoisomers, tautomers, N-oxides, hydrates, salts, solvates and solvates of the salts thereof, and also the compounds encompassed by the formula (I) which are specified hereinafter as working examples, and the stereoisomers, tautomers, N-oxides, hydrates, salts, solvates and solvates of the salts thereof.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

If, in the synthesis intermediates and working examples of the invention described below, a compound is given in the form of a salt of the corresponding base or acid, the exact stoichiometric composition of such a salt as obtained by the respective preparation and/or purification process is generally not known. Unless specified in more detail, additions to names and structural formulae, such as "hydrochloride", "trifluoroacetate", "sodium salt" or "x HCl", "x CF3COOH", "x Na+" are not to be understood stoichiometrically in the case of such salts, but have only descriptive character with regard to the salt-forming components comprised therein.

This applies correspondingly if synthesis intermediates or working examples or salts thereof were obtained by the preparation and/or purification processes described in the form of solvates, for example hydrates, whose stoichiometric composition (if of a defined type) is not known.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I, and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the inventive compounds may therefore in some cases also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

The present invention further provides all the possible crystalline and polymorphous forms of the compounds according to the invention, where the polymorphs may be present either as single polymorphs or as a mixture of a plurality of polymorphs in all concentration ranges.

In addition, the present invention also encompasses prodrugs of the compounds according to the invention. The term "prodrugs" here denotes compounds which may themselves be biologically active or inactive, but are converted (for example by metabolic or hydrolytic means) to inventive compounds during their residence time in the body.

The compounds according to the invention are novel and have antagonistic activity at the EP4 receptor and serve inter alia for treating endometriosis.

In the context of the present invention, unless specified otherwise, the substituents are defined as follows:

Alkyl represents a straight-chain or branched, saturated, monovalent hydrocarbon radical having at least 1 and at most 7 carbon atoms ($C_1$-$C_7$-alkyl). Any limitation of the range for the number of carbon atoms is evident from the prefix preceding "alkyl"; for example, $C_1$-$C_3$-alkyl means that only alkyl groups having 1, 2 or 3 carbon atoms are allowed.

Examples include: methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, 1,2-dimethylbutyl. The alkyl radicals may optionally be mono- or polysubstituted by fluorine.

Alkenyl and alkynyl denote straight-chain or branched unsaturated monovalent hydrocarbon radicals derived from the alkyl groups mentioned above in that the radical has at least two carbon atoms and that a single bond between two carbon atoms having a suitable number of hydrogen atoms is replaced by a double bond or a triple bond. Examples include: vinyl, allyl, buten-1-yl for alkenyl and ethynyl, propargyl, pentyn-1-yl for alkynyl. The number of carbon atoms is indicated by the prefix; for example, $C_2$-$C_5$-alkenyl denotes an alkenyl group having 2 to 5 carbon atoms.

Alkoxy represents a straight-chain or branched saturated alkyl ether radical of the formula alkyl-O— having at least 1 and at most 7 carbon atoms ($C_1$-$C_7$-alkoxy). Examples include: methoxy, ethoxy, n-propoxy, isopropoxy, n-butoxy, sec-butoxy, isobutoxy, tert-butoxy, pentyloxy, hexyloxy and heptyloxy.

The alkoxy radicals may optionally be mono- or polysubstituted by fluorine.

Alkoxyalkyl represents an alkoxy-substituted alkyl radical where $C_n$-alkoxy-$C_m$-alkyl means that the alkoxy moiety has n carbon atoms and the alkyl moiety via which the radical is attached has m carbon atoms. For example, ($C_1$-$C_5$-alkoxy)-($C_1$-$C_3$-alkyl) means that 1, 2, 3, 4 or 5 carbon atoms are allowed for the alkoxy group and 1, 2 or 3 carbon atoms are allowed for the alkyl groups.

Examples include: methoxymethyl, ethoxymethyl, propoxymethyl, isopropoxymethyl, 2-methoxyethyl, 2-ethoxyethyl, 2-propoxyethyl, 2-isopropoxyethyl.

$C_3$-$C_7$-Cycloalkyl denotes monocyclic alkyl radicals having 3 to 7 carbon atoms, where the number of the ring atoms may be modified as indicated in the indices ($C_4$-$C_6$-cycloalkyl, for example, means 4 or 5 ring atoms).

Examples include: cyclopropyl, cyclobutyl, cyclopentyl and cyclohexyl. The cycloalkyl radicals may optionally be mono- or polysubstituted by fluorine.

Cycloalkoxy represents a radical $C_3$-$C_6$-cycloalkyl-O, where $C_3$-$C_6$-cycloalkyl has the meaning given above.

Examples include: cyclopropyloxy, cyclobutyloxy, cyclopentyloxy and cyclohexyloxy.

Cycloalkoxyalkyl represents a cycloalkoxy-substituted alkyl radical where $C_n$-cycloalkoxy-$C_m$-alkyl means that the cycloalkoxy moiety has n carbon atoms and the alkyl moiety via which the radical is attached has m carbon atoms. For example, ($C_3$-$C_6$-cycloalkoxy)-($C_1$-$C_3$-alkyl) means that 3, 4, 5 or 6 carbon atoms are allowed for the cycloalkoxy group and 1, 2 or 3 carbon atoms are allowed for the alkyl groups.

Examples include: (cyclopropyloxy)methyl, (cyclobutyloxy)methyl, 2-(cyclopropyloxy)ethyl, 2-(cyclobutyloxy)ethyl.

Heterocycloalkyl or heterocyclyl denote monocyclic or bicyclic non-aromatic heterocyclic radicals having generally 4 to 10 ring atoms and up to 3, preferably up to 2, heteroatoms and/or heterogroups from the group consisting of N, O, S, SO, $SO_2$. The heterocyclyl radicals can be saturated or partially unsaturated. The binding valency can be at any carbon atom or at a nitrogen atom. 4- to 6-membered heterocyclyl denotes non-aromatic heterocyclic radicals having 4, 5 or 6 ring atoms and 1 or 2 heteroatoms and/or heterogroups from the group consisting of N, O, S, SO, $SO_2$.

Examples include: azetidinyl, pyrrolidinyl, piperidinyl, piperazinyl, 1,4-diazepanyl, morpholinyl, thiomorpholinyl, oxetanyl, tetrahydrofuranyl, tetrahydropyranyl, 1,4-dioxanyl, 2-oxooxazolidinyl. The heterocyclyl radicals may optionally be mono- or polysubstituted by fluorine, hydroxyl, methoxy and/or oxo.

Halogen is in each case to be understood as meaning fluorine, chlorine or bromine.

Heteroaryl denotes a mono- or bicyclic aromatic ring system which may in each case have 5-10 ring atoms and which, instead of the carbon, contains one or more identical or different heteroatoms such as oxygen, sulphur or nitrogen. The binding valency can be at any carbon atom or at a nitrogen atom. 5- or 6-membered heteroaryl denotes a monocyclic aromatic ring system which contains 5 or 6 ring atoms and which, instead of the carbon, contains one or more identical or different heteroatoms such as oxygen, sulphur or nitrogen. The binding valency can be at any carbon atom or at a nitrogen atom.

Examples include: thienyl, thiazolyl, furyl, pyrrolyl, oxazolyl, imidazolyl, pyrazolyl, isoxazolyl, isothiazolyl, oxadiazolyl, triazolyl, thiadiazolyl, tetrazolyl, pyridyl, pyridazinyl, pyrimidinyl, pyrazinyl, triazinyl, phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, isoquinolinyl, quinolinyl, quinolizinyl, quinazolinyl, quinoxalinyl, cinnolinyl, phthalazinyl, 1,7- or 1,8-naphthyridinyl, pteridinyl.

The $C_5$-$C_6$-membered heteroaryl radical may optionally be monosubstituted by fluorine, chlorine, hydroxy, $C_1$-$C_3$-alkyl and/or a trifluoromethyl group.

If a basic function is present, the physiologically acceptable salts of organic and inorganic acids such as hydrochloric acid, sulphuric acid, phosphoric acid, citric acid, tartaric acid, inter alia, are suitable.

Preference is given to compounds of the formula I where A represents cyano, $C_1$-$C_3$-alkyl, 5-membered heterocyclyl, 5-membered heteroaryl,
$R^{11}O$—$C(=O)$—$(CH_2)_p$—, $R^5R^{5'}N$—$C(=O)$—$(CH_2)_p$— or $R^5R^{5'}N$—$S(=O)_2$—$(CH_2)_p$—,
where heteroaryl is preferably selected from the group consisting of triazolyl, tetrazolyl and oxadiazolyl, and
where alkyl radicals may optionally be mono- or polysubstituted by identical or different hydroxy substituents,
and
where heteroaryl radicals may optionally be mono- or polysubstituted by identical or different $C_1$-$C_3$-alkyl, trifluoromethyl or hydroxy substituents,
B represents a group

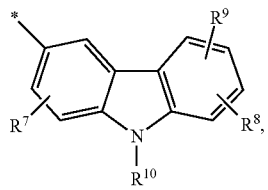

where * denotes the point of attachment in the molecule,
$R^{1a}$ represents hydrogen or $C_1$-$C_5$-alkyl,
$R^{1b}$ represents hydrogen, $C_1$-$C_5$-alkyl, $C_2$-$C_5$-alkenyl, ($C_3$-$C_6$-cycloalkyl)-$(CH_2)_m$—, (4- to 6-membered heterocyclyl)-$(CH_2)_n$—, ($C_1$-$C_5$-alkoxy)-($C_1$-$C_3$-alkyl)- or $(C_1$-$C_5$-alkyl)_{2N}$-($C_1$-$C_3$-alkyl)-,
where heterocyclyl is preferably selected from the group consisting of oxetanyl, tetrahydrofuranyl, 1,4-dioxanyl, morpholinyl and pyrrolidinyl,
and
where alkyl radicals and cycloalkyl radicals may optionally be mono- or polysubstituted by identical or different $C_1$-$C_5$-alkyl, hydroxy or ($C_1$-$C_5$-alkyl)-$S(O)_2$— radicals,
$R^4$ represents hydrogen, fluorine, chlorine, $C_1$-$C_2$-alkyl or $C_1$-$C_2$-alkoxy,
$R^5$, $R^{5'}$ independently of one another represent hydrogen, $C_1$-$C_7$-alkyl, (4- to 6-membered heterocyclyl)-$(CH_2)_r$—, ($C_1$-$C_7$-alkyl)-$S(O)_2$—, ($C_3$-$C_7$-cycloalkyl)-$S(O)_2$—, phenyl-$(CH_2)_r$—$S(O)_2$— or pyridyl-$(CH_2)_r$—$S(O)_2$—,
where heterocyclyl is preferably selected from the group consisting of morpholinyl and pyrrolidinyl,
and
where $R^5$ and $R^{5'}$ independently of one another may be mono- or polysubstituted by identical or different halogen, $C_1$-$C_2$-alkyl, trifluoromethyl, $(C_1$-$C_5$-alkyl)_2N$—, $C_1$-$C_2$-alkoxy or trifluoromethoxy substituents, or
$R^5$, $R^{5'}$ together with the nitrogen atom to which they are attached form a 4- to 6-membered heterocyclic ring which may optionally be substituted by oxo or hydroxy,
where a 6-membered heterocyclic ring may optionally contain, as a further ring atom, an oxygen atom,
$R^6$ represents hydrogen, fluorine, methyl or methoxy,
$R^7$ represents hydrogen, fluorine, chlorine, $C_1$-$C_3$-alkyl or $C_1$-$C_2$-alkoxy,
$R^8$ represents fluorine, chlorine, bromine, $C_1$-$C_3$-alkyl or $C_1$-$C_2$-alkoxy,
$R^9$ represents fluorine, chlorine, bromine, $C_1$-$C_3$-alkyl or $C_1$-$C_2$-alkoxy, or
$R^9$ represents bromine and simultaneously $R^8$ represents hydrogen,
$R_{10}$ represents $C_1$-$C_5$-alkyl, $C_3$-$C_5$-alkenyl, $C_3$-$C_5$-alkynyl, ($C_3$-$C_6$-cycloalkyl)-$(CH_2)_n$— or ($C_1$-$C_7$-alkoxy)-($C_2$-$C_5$-alkyl)-,
$R^{11}$ represents hydrogen or $C_1$-$C_7$-alkyl,
m is 0 or 1,
n is 0 or 1,
p is 0 and
r is 0, 1 or 2,
and diastereomers, enantiomers, solvates and salts or cyclodextrin clathrates thereof.

Preference is given to compounds of the formula I where A represents 5-membered heteroaryl, $R^{11}O$—$C(=O)$—$(CH_2)_p$—, $R^5R^{5'}N$—$C(=O)$—$(CH_2)_p$— or $R^5R^{5'}N$—$S(=O)_2$—$(CH_2)_p$—,
where heteroaryl is preferably selected from the group consisting of triazolyl, tetrazolyl and oxadiazolyl, and
where heteroaryl radicals may optionally be mono- or polysubstituted by identical or different $C_1$-$C_3$-alkyl, trifluoromethyl or hydroxy substituents,
B represents a group

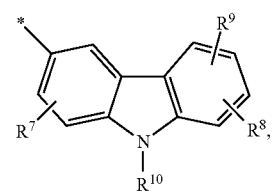

where * denotes the point of attachment in the molecule,
$R^{1a}$ represents hydrogen or methyl, $R^{1b}$ represents hydrogen, $C_1$-$C_2$-alkyl, vinyl, cyclopropyl-$(CH_2)_m$—, methoxy-($C_1$-$C_2$-alkyl)- or (N,N-dimethylamino)methyl, where alkyl radicals and cycloalkyl radicals may optionally be mono- or polysubstituted by identical or different methyl, hydroxy or methylsulphonyl substituents, $R^4$ represents hydrogen, fluorine, chlorine, methyl or methoxy, $R^5$, $R^{5'}$ independently of one another represent hydrogen, $C_1$-$C_2$-alkyl or (5- or 6-membered heterocyclyl)-$(CH_2)_r$—, where heterocyclyl is preferably selected from the group consisting of morpholinyl and pyrrolidinyl, and where $R^5$ and $R^{5'}$ independently of one another may optionally be mono- or polysubstituted by identical or different chlorine, fluorine, methyl, trifluoromethyl, N,N-dimethylamino, methoxy or trifluoromethoxy substituents, or $R^5$, $R^{5'}$ together with the nitrogen atom to which they are attached form a 4- to 6-membered heterocyclic ring which may optionally be substituted by oxo or hydroxy, where a 6-membered heterocyclic ring may optionally contain, as a further ring atom, an oxygen atom, $R^6$ represents hydrogen, fluorine, methyl or methoxy, $R^7$ represents hydrogen, fluorine, chlorine, methyl or methoxy, $R^8$ represents fluorine, chlorine, bromine, methyl or methoxy, $R^9$ represents fluorine, chlorine, bromine, methyl or methoxy, or $R^9$ represents bromine and simultaneously $R^8$ represents hydrogen, $R^{10}$ represents $C_1$-$C_3$-alkyl, allyl, propargyl, ($C_3$-$C_4$-cycloalkyl)-$(CH_2)_n$— or methoxyethyl, $R_{11}$ represents hydrogen or $C_1$-$C_3$-alkyl, m is 0 or 1, n is 0 or 1, p is 0 and r is 0, 1 or 2, and diastereomers, enantiomers, solvates and salts or cyclodextrin clathrates thereof.

Preference is given to compounds of the formula I where A represents $R^{11}O$—C(=O)—$(CH_2)_p$—, B represents a group

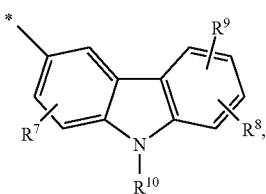

where * denotes the point of attachment in the molecule, $R^{1a}$ represents hydrogen, $R^{1b}$ represents methoxymethyl, $R^4$ represents hydrogen, fluorine or methyl, $R^6$ represents hydrogen, $R^7$ represents hydrogen, $R^8$ represents fluorine, chlorine or methyl, $R^9$ represents fluorine, chlorine, bromine or methyl, or $R^9$ represents bromine and simultaneously $R^8$ represents hydrogen, $R^{10}$ represents ethyl, $R^{11}$ represents hydrogen, methyl or ethyl, and p is 0, and diastereomers, enantiomers, solvates and salts or cyclodextrin clathrates thereof.

Preference is given to compounds of the formula I in which

A represents hydrogen, bromine, cyano, formyl, $C_1$-$C_3$-alkyl, 4- to 6-membered heterocyclyl, 5- to 6-membered heteroaryl, $R^{11}O$—C(=O)—$(CH_2)_p$—, $R^5R^{5'}N$—C(=O)—$(CH_2)_p$—, $R^{11}O$—S(=O)$_2$—$(CH_2)_p$—, $R^5R^{5'}N$—S(=O)$_2$—$(CH_2)_p$—, ($C_1$-$C_6$-alkyl)-S(=O)$_2$—, ($C_1$-$C_6$-alkyl)-S(=O)(=NH)— or ($C_3$-$C_6$-cycloalkyl)-S(=O)(=NH)—, where heteroaryl is preferably selected from the group consisting of pyrazolyl, imidazolyl, triazolyl, tetrazolyl, oxazolyl, isoxazolyl and oxadiazolyl, and where alkyl radicals may optionally be mono- or polysubstituted by identical or different halogen or hydroxy substituents, and where heterocyclyl radicals may optionally be mono- or polysubstituted by identical or different $C_1$-$C_3$-alkyl, trifluoromethyl or hydroxy substituents, and where heteroaryl radicals may optionally be mono- or polysubstituted by identical or different $C_1$-$C_3$-alkyl, trifluoromethyl or hydroxy substituents.

Preference is given to compounds of the formula I in which

A represents cyano, $C_1$-$C_3$-alkyl, 5-membered heterocyclyl, 5-membered heteroaryl, $R^{11}O$—C(=O)—$(CH_2)_p$—, $R^5R^{5'}N$—C(=O)—$(CH_2)_p$— or $R^5R^{5'}N$—S(=O)$_2$—$(CH_2)_p$—, where heteroaryl is preferably selected from the group consisting of triazolyl, tetrazolyl and oxadiazolyl, and where alkyl radicals may optionally be mono- or polysubstituted by identical or different hydroxy substituents, and where heteroaryl radicals may optionally be mono- or polysubstituted by identical or different $C_1$-$C_3$-alkyl, trifluoromethyl or hydroxy substituents.

Preference is given to compounds of the formula I in which

A represents 5-membered heteroaryl, $R^{11}O$—C(=O)—$(CH_2)_p$—, $R^5R^{5'}N$—C(=O)—$(CH_2)_p$— or $R^5R^{5'}N$—S(=O)$_2$—$(CH_2)_p$—, where heteroaryl is preferably selected from the group consisting of triazolyl, tetrazolyl and oxadiazolyl, and where heteroaryl radicals may optionally be mono- or polysubstituted by identical or different $C_1$-$C_3$-alkyl, trifluoromethyl or hydroxy substituents.

Preference is given to compounds of the formula I in which

A represents $R^{11}O-C(=O)-(CH_2)_p-$.

Preference is given to compounds of the formula I in which

B is selected from the following structures

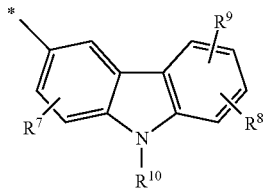

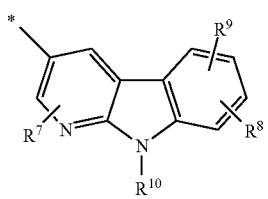

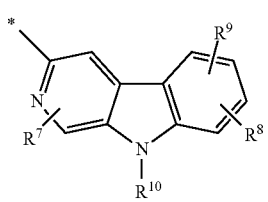

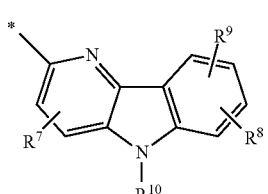

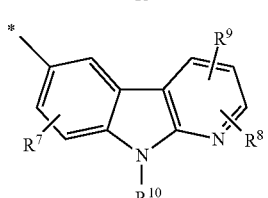

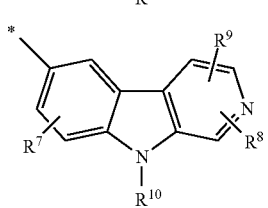

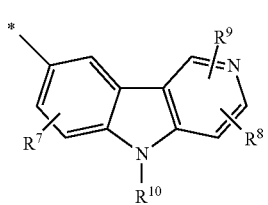

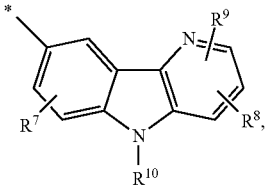

where * denotes the point of attachment in the molecule.

Preference is given to compounds of the formula I in which

B represents a group

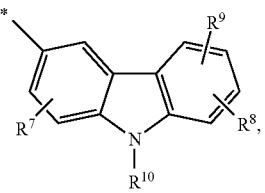

where * denotes the point of attachment in the molecule.

Preference is given to compounds of the formula I in which $R^{1a}$, $R^{1b}$ independently of one another represent hydrogen, cyano, $C_1$-$C_5$-alkyl, $C_2$-$C_5$-alkenyl, $C_2$-$C_5$-alkynyl, ($C_3$-$C_6$-cycloalkyl)-$(CH_2)_m$—, (4- to 6-membered heterocyclyl)-$(CH_2)_n$—, ($C_1$-$C_5$-alkoxy)-($C_1$-$C_3$-alkyl)-, ($C_3$-$C_6$-cycloalkoxy)-($C_1$-$C_3$-alkyl)-, $H_2N$—($C_1$-$C_3$-alkyl)-, ($C_1$-$C_5$-alkyl)NH—($C_1$-$C_3$-alkyl)- or ($C_1$-$C_5$-alkyl)$_2$N—($C_1$-$C_3$-alkyl)-, where heterocyclyl is preferably selected from the group consisting of oxetanyl, tetrahydrofuranyl, tetrahydropyranyl, 1,4-dioxanyl, morpholinyl, azetidinyl, pyrrolidinyl, piperazinyl and piperidinyl, and where alkyl radicals, cycloalkyl radicals and heterocyclyl radicals may optionally be mono- or polysubstituted by identical or different halogen, $C_1$-$C_5$-alkyl, hydroxy, $C(=O)OH$, $HO-C(=O)-(C_1-C_5\text{-alkyl})$-, $(C_1-C_5\text{-alkyl})O-C(=O)-(C_1-C_5\text{-alkyl})$- or $(C_1-C_5\text{-alkyl})$-$S(=O)_2$— substituents.

Preference is given to compounds of the formula I in which $R^{1a}$ represents hydrogen or $C_1$-$C_5$-alkyl.

Preference is given to compounds of the formula I in which $R^{1a}$ represents hydrogen or methyl.

Preference is given to compounds of the formula I in which $R^{1a}$ represents methyl.

Preference is given to compounds of the formula in I which $R^{1a}$ represents hydrogen.

Preference is given to compounds of the formula I in which $R^{1b}$ represents hydrogen, $C_1$-$C_5$-alkyl, $C_2$-$C_5$-alkenyl, ($C_3$-$C_6$-cycloalkyl)-$(CH_2)_m$—, (4- to 6-membered heterocyclyl)-$(CH_2)_n$—, ($C_1$-$C_5$-alkoxy)-($C_1$-$C_3$-alkyl)- or ($C_1$-$C_5$-alkyl)$_2$N—($C_1$-$C_3$-alkyl)-, where heterocyclyl is preferably selected from the group consisting of oxetanyl, tetrahydrofuranyl, 1,4-dioxanyl, morpholinyl and pyrrolidinyl,
and
where alkyl radicals and cycloalkyl radicals may optionally be mono- or polysubstituted by identical or different $C_1$-$C_5$-alkyl, hydroxy or ($C_1$-$C_5$-alkyl)-S(O)$_2$— radicals.

Preference is given to compounds of the formula I in which
$R^{1b}$ represents hydrogen, $C_1$-$C_2$-alkyl, vinyl, cyclopropyl-(CH$_2$)$_m$—, methoxy-($C_1$-$C_2$-alkyl)- or (N,N-dimethylamino)methyl,
where alkyl, alkylene and cycloalkyl radicals may optionally be mono- or polysubstituted by identical or different methyl, hydroxy or methylsulphonyl substituents.

Preference is given to compounds of the formula I in which
$R^{1b}$ represents methoxymethyl.

Preference is given to compounds of the formula I in which
$R^4$ represents hydrogen, fluorine, chlorine, $C_1$-$C_2$-alkyl, $C_3$-$C_5$-cycloalkyl, $C_1$-$C_2$-alkoxy or ($C_3$-$C_4$-cycloalkyl)-CH$_2$—,
where alkyl and cycloalkyl radicals may optionally be mono- or polysubstituted by identical or different halogen or hydroxy substituents.

Preference is given to compounds of the formula I in which
$R^4$ represents hydrogen, fluorine, chlorine, $C_1$-$C_2$-alkyl or $C_1$-$C_2$-alkoxy.

Preference is given to compounds of the formula I in which
$R^4$ represents hydrogen, fluorine, chlorine, methyl or methoxy.

Preference is given to compounds of the formula I in which
$R^4$ represents hydrogen, fluorine or methyl.

Preference is given to compounds of the formula I in which
$R^4$ represents hydrogen.

Preference is given to compounds of the formula I in which
$R^4$ represents fluorine.

Preference is given to compounds of the formula I in which
$R^4$ represents methyl.

Preference is given to compounds of the formula I in which
$R^5$, $R^{5'}$ independently of one another represent hydrogen, $C_1$-$C_7$-alkyl, ($C_1$-$C_7$-alkoxy)-($C_2$-$C_5$-alkyl)-, (4- to 6-membered heterocyclyl)-(CH$_2$)$_r$—, ($C_1$-$C_7$-alkyl)-C(=O)—, ($C_3$-$C_7$-cycloalkyl)-C(=O)—, phenyl-(CH$_2$)$_r$—C(=O)—, pyridyl-(CH$_2$)$_r$—C(=O)—, ($C_1$-$C_7$-alkyl)-S(=O)$_2$—, ($C_3$-$C_7$-cycloalkyl)-S(=O)$_2$—, phenyl-(CH$_2$)$_r$—S(=O)$_2$— or pyridyl-(CH$_2$)$_r$—S(=O)$_2$—,
where heterocyclyl is preferably selected from the group consisting of oxetanyl, tetrahydrofuranyl, tetrahydropyranyl, 1,4-dioxanyl, morpholinyl, azetidinyl, pyrrolidinyl, piperazinyl and piperidinyl,
and
where $R^5$ and $R^{5'}$ independently of one another may be mono- or polysubstituted by identical or different halogen, hydroxy, $C_1$-$C_2$-alkyl, trifluoromethyl, ($C_1$-$C_5$-alkyl)NH—, ($C_1$-$C_5$-alkyl)$_2$N—, $C_1$-$C_2$-alkoxy or trifluoromethoxy substituents,
or
$R^5$, $R^{5'}$ together with the nitrogen atom to which they are attached form a 4- to 6-membered heterocyclic ring which may optionally be mono- or polysubstituted by identical or different oxo, hydroxy, carboxy, $C_1$-$C_2$-alkyl
or
$C_1$-$C_2$-alkoxy substituents,
where a 6-membered heterocyclic ring may optionally contain, as further ring atom, a heteroatom selected from the group consisting of O and N.

Preference is given to compounds of the formula I in which
$R^5$, $R^{5'}$ independently of one another represent hydrogen, $C_1$-$C_7$-alkyl, ($C_1$-$C_7$-alkoxy)-($C_2$-$C_5$-alkyl)-, (4- to 6-membered heterocyclyl)-(CH$_2$)$_r$—, ($C_1$-$C_7$-alkyl)-C(=O)—, ($C_3$-$C_7$-cycloalkyl)-C(=O)—, phenyl-(CH$_2$)$_r$—C(=O)—, pyridyl-(CH$_2$)$_r$—C(=O)—, ($C_1$-$C_7$-alkyl)-S(=O)$_2$—, ($C_3$-$C_7$-cycloalkyl)-S(=O)$_2$—, phenyl-(CH$_2$)$_r$—S(=O)$_2$— or pyridyl-(CH$_2$)$_r$—S(=O)$_2$—,
where heterocyclyl is preferably selected from the group consisting of oxetanyl, tetrahydrofuranyl, tetrahydropyranyl, 1,4-dioxanyl, morpholinyl, azetidinyl, pyrrolidinyl, piperazinyl and piperidinyl,
and
where $R^5$ and $R^{5'}$ independently of one another may be mono- or polysubstituted by identical or different halogen, hydroxy, $C_1$-$C_2$-alkyl, trifluoromethyl, ($C_1$-$C_5$-alkyl)NH—, ($C_1$-$C_5$-alkyl)$_2$N—, $C_1$-$C_2$-alkoxy or trifluoromethoxy substituents.

Preference is given to compounds of the formula I in which
$R^5$, $R^{5'}$ together with the nitrogen atom to which they are attached form a 4- to 6-membered heterocyclic ring which may optionally be mono- or polysubstituted by identical or different oxo, hydroxy, carboxy, $C_1$-$C_2$-alkyl
or
$C_1$-$C_2$-alkoxy substituents,
where a 6-membered heterocyclic ring may optionally contain, as further ring atom, a heteroatom selected from the group consisting of O and N.

Preference is given to compounds of the formula I in which
$R^5$, $R^{5'}$ independently of one another represent hydrogen, $C_1$-$C_7$-alkyl, (4- to 6-membered heterocyclyl)-(CH$_2$)$_r$—, ($C_1$-$C_7$-alkyl)-S(O)$_2$—, ($C_3$-$C_7$-cycloalkyl)-S(O)$_2$—, phenyl-(CH$_2$)$_r$—S(O)$_2$— or pyridyl-(CH$_2$)$_r$—S(O)$_2$—,
where heterocyclyl is preferably selected from the group consisting of morpholinyl and pyrrolidinyl,
and
where $R^5$ and $R^{5'}$ independently of one another may be mono- or polysubstituted by identical or different halogen, $C_1$-$C_2$-alkyl, trifluoromethyl, ($C_1$-$C_5$-alkyl)$_2$N—, $C_1$-$C_2$-alkoxy or trifluoromethoxy,
or
$R^5$, $R^{5'}$ together with the nitrogen atom to which they are attached form a 4- to 6-membered heterocyclic ring which may optionally be substituted by oxo or hydroxy,
where a 6-membered heterocyclic ring may optionally contain, as a further ring atom, an oxygen atom.

Preference is given to compounds of the formula I in which
$R^5$, $R^{5'}$ independently of one another represent hydrogen, $C_1$-$C_7$-alkyl, (4- to 6-membered heterocyclyl)-(CH$_2$)$_r$—, ($C_1$-$C_7$-alkyl)-S(O)$_2$—, ($C_3$-$C_7$-cycloalkyl)-S(O)$_2$—, phenyl-(CH$_2$)$_r$—S(O)$_2$— or pyridyl-(CH$_2$)$_r$—S(O)$_2$—,
where heterocyclyl is preferably selected from the group consisting of morpholinyl and pyrrolidinyl,
and
where $R^5$ and $R^{5'}$ independently of one another may be mono- or polysubstituted by identical or different halogen, $C_1$-$C_2$-alkyl, trifluoromethyl, ($C_1$-$C_5$-alkyl)$_2$N—, $C_1$-$C_2$-alkoxy or trifluoromethoxy substituents.

Preference is given to compounds of the formula I in which
$R^5$, $R^{5'}$ together with the nitrogen atom to which they are attached form a 4- to 6-membered heterocyclic ring which may optionally be substituted by oxo or hydroxy,
where a 6-membered heterocyclic ring may optionally contain, as a further ring atom, an oxygen atom.

Preference is given to compounds of the formula I in which
$R^5$, $R^{5'}$ independently of one another represent hydrogen, $C_1$-$C_2$-alkyl or (5- or 6-membered heterocyclyl)-(CH$_2$)$_r$—,
where heterocyclyl is preferably selected from the group consisting of morpholinyl and pyrrolidinyl,
and
where $R^5$ and $R^{5'}$ independently of one another may optionally be mono- or polysubstituted by identical or different chlorine, fluorine, methyl, trifluoromethyl, N,N-dimethylamino, methoxy or trifluoromethoxy substituents.

Preference is given to compounds of the formula I in which
$R^6$ represents hydrogen, fluorine, chlorine, methyl, trifluoromethyl, methoxy or trifluoromethoxy.

Preference is given to compounds of the formula I in which
$R^6$ represents hydrogen, fluorine, methyl or methoxy.

Preference is given to compounds of the formula I in which
$R^6$ represents hydrogen.

Preference is given to compounds of the formula I in which
$R^7$ represents hydrogen, fluorine, chlorine, cyano, SF$_5$, $C_1$-$C_3$-alkyl, $C_3$-$C_5$-cycloalkyl, $C_1$-$C_2$-alkoxy or ($C_3$-$C_4$-cycloalkyl)-CH$_2$—,
where alkyl and cycloalkyl radicals may optionally by mono- or polysubstituted by identical or different halogen radicals.

Preference is given to compounds of the formula I in which
$R^7$ represents hydrogen, fluorine, chlorine, $C_1$-$C_3$-alkyl or $C_1$-$C_2$-alkoxy.

Preference is given to compounds of the formula I in which
$R^7$ represents hydrogen, fluorine, chlorine, methyl or methoxy.

Preference is given to compounds of the formula I in which
$R^7$ represents hydrogen.

Preference is given to compounds of the formula I in which
$R^8$ represents fluorine, chlorine, bromine, cyano, SF$_5$, $C_1$-$C_3$-alkyl, $C_3$-$C_5$-cycloalkyl, $C_1$-$C_2$-alkoxy or ($C_3$-$C_4$-cycloalkyl)-CH$_2$—,
where alkyl and cycloalkyl radicals may optionally be mono- or polysubstituted by identical or different halogen radicals.

Preference is given to compounds of the formula I in which
$R^8$ represents fluorine, chlorine, bromine, $C_1$-$C_3$-alkyl or $C_1$-$C_2$-alkoxy.

Preference is given to compounds of the formula I in which
$R^8$ represents fluorine, chlorine, bromine, methyl or methoxy.

Preference is given to compounds of the formula I in which
$R^8$ represents fluorine, chlorine or methyl.

Preference is given to compounds of the formula I in which
$R^8$ represents fluorine.

Preference is given to compounds of the formula I in which
$R^8$ represents chlorine.

Preference is given to compounds of the formula I in which
$R^8$ represents methyl.

Preference is given to compounds of the formula I in which
$R^9$ represents fluorine, chlorine, bromine, cyano, $C_1$-$C_3$-alkyl or $C_1$-$C_2$-alkoxy.

Preference is given to compounds of the formula I in which
$R^9$ represents fluorine, chlorine, bromine, $C_1$-$C_3$-alkyl or $C_1$-$C_2$-alkoxy.

Preference is given to compounds of the formula I in which
$R^9$ represents fluorine, chlorine, bromine, methyl or methoxy.

Preference is given to compounds of the formula I in which
$R^9$ represents fluorine, chlorine, bromine or methyl.

Preference is given to compounds of the formula I in which
$R^9$ represents fluorine.

Preference is given to compounds of the formula I in which
$R^9$ represents chlorine.

Preference is given to compounds of the formula I in which
$R^9$ represents bromine.

Preference is given to compounds of the formula I in which
$R^9$ represents methyl.

Preference is given to compounds of the formula I in which
$R^9$ represents bromine and simultaneously $R^8$ represents hydrogen.

Preference is given to compounds of the formula I in which
$R^{10}$ represents $C_1$-$C_5$-alkyl, $C_3$-$C_5$-alkenyl, $C_3$-$C_5$-alkynyl, ($C_3$-$C_6$-cycloalkyl)-(CH$_2$)$_n$—, (4- to 6-membered heterocyclyl)-(CH$_2$)$_n$— or ($C_1$-$C_7$-alkoxy)-($C_2$-$C_5$-alkyl)-,
where heterocyclyl is preferably selected from the group consisting of oxetanyl, tetrahydrofuranyl, tetrahydropyranyl, morpholinyl, pyrrolidinyl and piperidinyl
and
where alkyl radicals, cycloalkyl radicals and heterocyclyl radicals may optionally be mono- or polysubstituted by identical or different halogen, $C_1$-$C_2$-alkyl, $C_1$-$C_2$-alkoxy or C(=O)OH radicals.

Preference is given to compounds of the formula I in which
$R^{10}$ represents $C_1$-$C_5$-alkyl, $C_3$-$C_5$-alkenyl, $C_3$-$C_5$-alkynyl, ($C_3$-$C_6$-cycloalkyl)-$(CH_2)_n$— or ($C_1$-$C_7$-alkoxy)-($C_2$-$C_5$-alkyl)-.

Preference is given to compounds of the formula I in which
$R^{10}$ represents $C_1$-$C_3$-alkyl, allyl, propargyl, ($C_3$-$C_4$-cycloalkyl)-$(CH_2)_n$— or methoxyethyl.

Preference is given to compounds of the formula I in which
$R^{10}$ represents ethyl.

Preference is given to compounds of the formula I in which
$R^{11}$ represents hydrogen, $C_1$-$C_7$-alkyl, $C_3$-$C_7$-cycloalkyl, phenyl-$(CH_2)_q$— or ($C_1$-$C_7$-alkoxy)-($C_2$-$C_5$-alkyl)-,
where phenyl may optionally be mono- or polysubstituted by identical or different $C_1$-$C_3$-alkyl, trifluoromethyl or hydroxy radicals.

Preference is given to compounds of the formula I in which
$R^{11}$ represents hydrogen or $C_1$-$C_7$-alkyl.

Preference is given to compounds of the formula I in which
$R^{11}$ represents hydrogen or $C_1$-$C_3$-alkyl.

Preference is given to compounds of the formula I in which
$R^{11}$ represents hydrogen, methyl or ethyl.

Preference is given to compounds of the formula I in which
$R^{11}$ represents methyl or ethyl.

Preference is given to compounds of the formula I in which
$R^{11}$ represents hydrogen.

Preference is given to compounds of the formula I in which
m is 0, 1, 2 or 3.

Preference is given to compounds of the formula I in which
m is 0 or 1.

Preference is given to compounds of the formula I in which
m is 1.

Preference is given to compounds of the formula I in which
m is 0.

Preference is given to compounds of the formula I in which
n is 0, 1, 2 or 3.

Preference is given to compounds of the formula I in which
n is 0 or 1.

Preference is given to compounds of the formula I in which
n is 1.

Preference is given to compounds of the formula I in which
n is 0.

Preference is given to compounds of the formula I in which
p is 0, 1 or 2.

Preference is given to compounds of the formula I in which
p is 0.

Preference is given to compounds of the formula I in which
q is 1, 2 or 3.

Preference is given to compounds of the formula I in which
r is 0, 1, 2 or 3.

Preference is given to compounds of the formula I in which
r is 0, 1 or 2.

The following compounds according to the present invention are very particularly preferred:
1. Methyl 2-(6-bromo-9-ethyl-9H-carbazol-3-yl)-1-(2-methoxyethyl)-4-methyl-1H-benzimidazole-5-carboxylate
2. 2-(6-Bromo-9-ethyl-9H-carbazol-3-yl)-1-(2-methoxyethyl)-4-methyl-1H-benzimidazole-5-carboxylic acid
3. Methyl 2-(9-ethyl-8-fluoro-6-methyl-9H-carbazol-3-yl)-1-(2-methoxyethyl)-4-methyl-1H-benzimidazole-5-carboxylate
4. 2-(9-Ethyl-8-fluoro-6-methyl-9H-carbazol-3-yl)-1-(2-methoxyethyl)-4-methyl-1H-benzimidazole-5-carboxylic acid
5. Methyl 2-(9-ethyl-6-fluoro-8-methyl-9H-carbazol-3-yl)-1-(2-methoxyethyl)-4-methyl-1H-benzimidazole-5-carboxylate
6. 2-(9-Ethyl-6-fluoro-8-methyl-9H-carbazol-3-yl)-1-(2-methoxyethyl)-4-methyl-1H-benzimidazole-5-carboxylic acid
7. 2-(9-Ethyl-6-fluoro-8-methyl-9H-carbazol-3-yl)-4-fluoro-1-(2-methoxyethyl)-1H-benzimidazole-5-carboxylic acid
8. 2-(9-Ethyl-8-fluoro-6-methyl-9H-carbazol-3-yl)-4-fluoro-1-(2-methoxyethyl)-1H-benzimidazole-5-carboxylic acid
9. Ethyl 2-(9-ethyl-8-fluoro-6-methyl-9H-carbazol-3-yl)-1-(2-methoxyethyl)-1H-benzimidazole-5-carboxylate
10. 2-(9-Ethyl-8-fluoro-6-methyl-9H-carbazol-3-yl)-1-(2-methoxyethyl)-1H-benzimidazole-5-carboxylic acid
11. Methyl 2-(8-chloro-9-ethyl-6-methyl-9H-carbazol-3-yl)-1-(2-methoxyethyl)-4-methyl-1H-benzimidazole-5-carboxylate
12. 2-(8-Chloro-9-ethyl-6-methyl-9H-carbazol-3-yl)-1-(2-methoxyethyl)-4-methyl-1H-benzimidazole-5-carboxylic acid
13. 2-(5-Chloro-9-ethyl-6-methyl-9H-carbazol-3-yl)-1-(2-methoxyethyl)-4-methyl-1H-benzimidazole-5-carboxylic acid The present invention provides the compounds of the formula (I) for treatment and/or prophylaxis of diseases.

The compounds of the general formula I according to the invention are ligands of the EP4 receptor and have antagonistic activity.

Accordingly, the present invention provides compounds of the formula (I) which act antagonistically at the EP4 receptor for the treatment and/or prophylaxis of endometriosis, of uterine leiomyomas, of uterine menstrual complaints, where the menstrual complaints may be heavy and prolonged menorrhoea, irregular menorrhoea and pain, of dysmenorrhoea, of cancer, where the cancer may be lung cancer, cancer of the intestine, breast cancer, skin cancer, prostate cancer, cancer of the oesophagus and leukaemia, of arteriosclerosis and of polycystic kidney disorders.

The present application furthermore provides the use of a compound according to formula (I) for preparing a medicament for the treatment and/or prophylaxis of diseases.

This may be the treatment and/or prophylaxis of endometriosis, of uterine leiomyomas, of uterine menstrual complaints, where the menstrual complaints may be heavy and prolonged menorrhoea, irregular menorrhoea and pain, of dysmenorrhoea, of cancer, where the cancer may be lung cancer, cancer of the intestine, breast cancer, skin cancer, prostate cancer, cancer of the oesophagus and leukaemia, of arteriosclerosis and of polycystic kidney disorders.

The antagonistic action can be determined by an antagonism assay (see Example 3.2.1 of the biological examples). Thus, for example, compound 10 according to the invention inhibits the stimulation of cAMP production, induced by administration of PGE2 to cells expressing the EP4 receptor, with an $IC_{50}$ of about 1.5 nM.

Antagonists are to be understood as meaning molecules which bind to their respective receptors and which inhibit initiation of the signal transduction path(s) coupled to the receptor by the natural ligand(s). Usually, the antagonists compete with the natural ligand of the receptor for receptor binding. However, other modifications of the receptor by molecules which prevent activation of receptor-coupled signal transduction paths by the natural ligand(s) are possible (e.g. non-competitive allosteric modifications of the receptor).

Preferably, the antagonists bind reversibly to their corresponding receptors.

The EP4 receptor ligands with antagonistic action have preferred affinity for the EP4 receptor as compared to any other EP subtype. The antagonism is measured in the presence of the natural agonist (PGE2).

Also subject matter of the present invention owing to the antagonistic action at the EP4 receptor are medicaments for the treatment and/or prophylaxis of disorders including infectious disorders, cancer, cardiovascular disorders, angiogenetic disorders, impaired uterine contractions, acute and chronic pain, inflammatory disorders, neuroinflammatory disorders, neurodegenerative disorders, autoimmune disorders, immune-dependent disorders/therapies, nephrological disorders, ophthalmological disorders.

Infectious disorders are to be understood as meaning disorders caused by unicellular parasites (e.g. *Klebsiella, Streptococcus*). In the case of infectious disorders, the medicaments may act immunomodulatory such that the disorders can be treated prophylactically (reduction of the risk of infection, for example in bone marrow transplantations) or therapeutically. Cancer is to be understood as meaning solid tumours and leukaemias; viral infections are to be understood as meaning, e.g., cytomegalus infections, hepatitis, hepatitis B and C and HIV diseases; cardiovascular diseases are to be understood as meaning ischaemic reperfusion disease, stenoses, arterioscleroses, restenoses, arthritis, Kawasaki syndrome and aneurysms; angiogenetic diseases are to be understood, in addition to endometriosis, as meaning fibrosis and fibroids in the uterus; disorders of uterine contraction are to be understood as meaning, e.g., menstrual complaints; pain is to be understood as meaning, for example, inflammatory hyperalgesia, arthritis, arthrosis, neuropathic pain, gout, visceral pain, backache, headache, migraine, toothache, pain due to sunburn and pain due to burn injuries, inflammatory diseases are to be understood as meaning, for example, inflammatory bowel diseases; neuroinflammatory and neurodegenerative diseases are to be understood as meaning, e.g., multiple sclerosis, Alzheimer's, Parkinson's, ALS, stroke; immune-dependent diseases/therapies are to be understood as meaning, e.g., transplants, in which immunomodulation increases the therapeutic success; autoimmune diseases are to be understood as meaning, for example, the ophthalmological disease Basedow's disease, and nephrological diseases are to be understood as meaning polycystic kidney disorders, glomerulonephritis.

The compounds according to the invention can be mixed here with the customary pharmaceutical auxiliaries. The EP4 receptor ligands with antagonistic activity are formulated in a manner known per se to the person skilled in the art.

The present invention also relates to the use of a compound according to formula (I) for the production of a medicament.

The present invention also relates to medicaments comprising the compounds according to the invention, with suitable formulation substances and carriers.

The therapeutically active dose is dependent on the body weight, administration route, individual response, the type of preparation and time or interval at which administration takes place. A typical dose range for a woman of 70 kg body weight is between 1-500 mg/day, preferably between 5 and 20 mg/day.

The present invention further provides medicaments comprising at least one compound according to the invention and at least one or more than one further active compound, especially for treatment and/or prophylaxis of endometriosis. Preferred examples of suitable active compounds for combinations include: selective oestrogen receptor modulators (SERMs), oestrogen receptor (ER) antagonists, aromatase inhibitors, 17β-HSD1 inhibitors, steroid sulphatase (STS) inhibitors, GnRH agonists and antagonists, kisspeptin receptor (KISSR) antagonists, selective androgen receptor modulators (SARMs), androgens, 5α-reductase inhibitors, selective progesterone receptor modulators (SPRMs), gestagens, antigestagens, oral contraceptives, inhibitors of mitogen-activated protein (MAP) kinases and inhibitors of the MAP kinases (Mkk3/6, Mek1/2, Erk1/2), inhibitors of protein kinase B (PKBα/β/γ; Akt1/2/3), inhibitors of phosphoinositide 3-kinase (PI3K), inhibitors of cyclin-dependent kinase (CDK1/2), inhibitors of the hypoxia-induced signalling pathway (HIF1alpha inhibitors, activators of prolylhydroxylases), histone deacetylase (HDAC) inhibitors, prostaglandin F receptor (FP) (PTGFR) antagonists, neurokinin 1 receptor antagonists, paracetamol, selective COX2 inhibitors and/or non-selective COX1/COX2 inhibitors.

The invention also relates to pharmaceutical formulations comprising at least one compound of the general formula I (or physiologically acceptable addition salts with organic and inorganic acids) and to the use of these compounds for production of medicaments, especially for the aforementioned indications.

The compounds can be used for the aforementioned indications after either oral or parenteral administration.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in suitable administration forms for these administration routes.

The dosage of the compounds of the general formula I in these preparations should be 0.01%-20%, in order to achieve an adequate pharmacological action.

The dosage of the active compounds can vary, depending on administration route, age and weight of the patient, nature and severity of the disease to be treated and similar factors. The treatment can be carried out by means of individual doses or by a plurality of doses over a relatively long period. The daily dose is 0.5-1000 mg, preferably 50-200 mg, where the dose can be given as an individual dose to be administered once or subdivided into 2 or more daily doses.

As carrier systems, surface-active auxiliaries such as salts of the bile acids or animal or vegetable phospholipids can also be used, but also mixtures thereof and liposomes or their constituents.

The formulations and administration forms described above also form part of the subject-matter of the present invention.

If, in addition to the compound according to the invention according to formula I, further active compounds are contained, these can be formulated in a common administration form or optionally also administered as a combination preparation.

Suitable administration forms for oral administration are those which work according to the prior art and release the compounds to be used according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound to be used according to the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, tinctures, vaginal capsules and suppositories, tampons, intrauterine pessaries, aqueous suspensions (lotions, shaking mixtures), lipophilic suspensions, crystal suspensions, aqueous and oily injection solutions, depot preparations, ointments, fatty ointments, gels, creams, transdermal therapeutic systems (e.g. patches), milk, pastes, foams, dusting powders, implants, intrauterine spirals, vaginal rings or stents.

Oral and parenteral administration are preferred, especially oral and intravenous administration.

The compounds to be used according to the invention can be converted into the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

The present invention further provides medicaments which comprise at least one compound according to the invention, typically together with one or more inert, non-toxic, pharmaceutically suitable excipients, and the use thereof for the aforementioned purposes.

In the case of oral administration, the amount is about 0.01 to 100 mg/kg of body weight per day. The amount of a compound of the general formula I to be administered varies within a wide range and can cover any effective amount. Depending on the condition to be treated and the mode of administration, the amount of the compound administered may be 0.01-100 mg/kg of body weight per day.

It may nevertheless be necessary where appropriate to deviate from the stated amounts, specifically as a function of the body weight, route of administration, individual response to the active compound, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

Unless stated otherwise, the percentages in the tests and examples which follow are percentages by weight; parts are parts by weight. Solvent ratios, dilution ratios and concentration data for the liquid/liquid solutions are in each case based on volume.

Also part of the subject-matter of the present invention is the use of the substances according to the invention as EP4 receptor ligands with antagonistic action for the prophylaxis and direct treatment of disorders that are related causally to the EP4 receptor or of disorders that can be treated by influencing the EP4 receptor.

Prostaglandins play an important role in angiogenesis (Sales, Jabbour, 2003, Reproduction 126, 559-567; Kuwano et al., 2004, FASEB J. 18, 300-310; Kamiyama et al., 2006, Oncogene 25, 7019-7028; Chang et al., 2005, Prostaglandins & other Lipid Mediators 76, 48-58).

Prostaglandins play an important role in uterine contraction, contractions that are too strong are responsible for menstrual pains (Sales, Jabbour, 2003, Reproduction 126, 559-567). Prostaglandins and here especially the EP4 and the EP2 receptor have been associated with heavy menstrual bleeding (Smith et al., 2007 (Human Reproduction, Vol. 22, No. 5 pp. 1450-1456).

The present invention relates to the use of the substances of the general formula I for the prophylaxis and treatment of menstrual complaints and heavy menstrual bleeding and pain during menstruation.

Fibroids (myomas) are benign tumours in the uterus having a high prevalence rate. A connection to prostaglandin metabolism exists by way of the stimulation of aromatase by a PGE2/cAMP-mediated signal pathway, and by possible other mechanisms (Imir et al., 2007, J Clin Endocrinol Metab 92, 1979-1982).

The present invention relates to the use of the substances of the general formula I for the prophylaxis and treatment of fibroids (myomas).

Growing research results also confirm the importance of the EP receptors in a large number of types of cancer (e.g. breast cancer, colon cancer, lung cancer, prostate cancer, leukaemia, skin cancer), which suggests future possibilities of the use of modulators (antagonists or agonists) of the EP4 receptor for the treatment and prevention (prophylactic and/or adjuvant) of cancer (Fulton et al., 2006, Cancer Res; 66(20): 9794-7; Hull et al., 2004, Mol Cancer Ther; 3(8): 1031-9; Wang et al., 2004, Seminars in Oncology, Vol 31, No 1, Suppl 3: pp 64-73).

The present invention relates to the use of the substances of the general formula I for the treatment and prevention of cancers.

The activation of endothelial cells in the pathogenic process of arteriosclerosis plays an important role. Recent research shows an involvement of the EP4 receptor (Minami et al., 2008, J Biol Chem., April 11; 283(15):9692-703. Epub 2008 Feb. 12).

The present invention relates to the use of the substances of the general formula I for the treatment and prevention of arteriosclerosis.

Recent scientific publications show that in neurodegenerative, neuroinflammatory and ischaemic diseases (Alzheimer's, Parkinson's, ALS, stroke) prostaglandins and the EP4 receptor are important components of the disease process (Hoshino et al., 2007, J Biol Chem.; 282(45): 32676-88; Cimino et al., 2008, Current Medicinal Chemistry, 1863-1869).

Multiple sclerosis is a chronic inflammation of the nervous system. Prostaglandins, especially PGE2 and effects mediated by means of the EP4 receptor are causally associated with the pathological processes in multiple sclerosis (Palumbo et al., 2011, Prostaglandins, Leukotrienes and Essential Fatty Acids 85: 29-35; Kihara et al., 2009, Proc Natl Acad Sci U. S. A, 106, Nr. 51: 21807-21812).

The present invention relates to the use of the substances of the general formula I for the treatment and prevention of neurodegenerative, neuroinflammatory and ischaemic diseases such as, for example, Alzheimer's, Parkinson's, ALS, stroke and the treatment of multiple sclerosis.

Polycystic kidney disorders are likewise connected with the EP4 receptor (Liu et al., 2012, Am J Physiol Renal Physiol. 2012 Aug. 29. [Epub ahead of print.)

The present invention relates to the use of the substances of the general formula I for the treatment and prevention of polycystic kidney disorders.

There are indications that an inflammatory, increased sensitivity to pain can be treated by specifically modulating EP4 receptors. In addition, the EP4 receptor is connected with further types of pain (Zeilhofer, 2007, Biochemical Pharmacology 73; 165-174). Murase et al. (Eur J Pharmacol. 2008 Feb. 2; 580(1-2):116-21) report on a connection between EP4 receptor blockade and a symptomatic relief from the symptoms that occur in osteoarthritis and/or rheumatoid arthritis.

The present invention relates to the use of the substances according to the invention for the treatment and prevention of pain of differing origin such as, for example, inflammatory hyperalgesia or arthritis.

Recent scientific publications indicate a use of EP4 inhibitors for the prevention and/or treatment of infections of the airways. Serezani et al. (μm Respir Cell Mol Biol Vol 37. pp 562-570, 2007) describe that by means of the activation of the EP4 receptor by PGE2, macrophages of the respiratory tract are impaired in their ability to destroy bacteria. Bacterial infections lead to an increased production of prostaglandins, inter alfa PGE2, which, by means of this mechanism weakens the body's own defence against bacteria. As shown in this publication, this capability of bacterial control can be restored again by an inactivation of the EP4 receptor (and of the EP2 receptor).

The present invention relates to the use of the substances according to the invention for the prevention and treatment of infectious diseases of the lung.

Inflammatory bowel diseases (e.g. Crohn's disease) are likewise connected with the prostaglandin EP4 receptor (Sheibanie et al., 2007, The Journal of Immunology, 178: 8138-8147).

The present invention relates to the use of the substances according to the invention for the prevention and treatment of inflammatory bowel diseases.

In bone marrow transplants, complications due to infections often occur, an overproduction of PGE2 being connected with a reduced immune defence (Ballinger et al., 2006, The Journal of Immunology, 177: 5499-5508).

The present invention relates to the use of the substances according to the invention for prophylaxis and treatment in connection with bone marrow transplants.

Graves' disease is an autoimmune disease of the thyroid, in which the clinical picture can also comprise pathological changes in the eye (endocrine ophthalmopathy; prominence of the eyeballs (exophthalmos)). In this connection, immigrating lymphocytes activate existing fibroblasts, which leads, inter alia, to an accumulation of mucopolysaccharides. Possible consequences are impairments of vision up to blindness. Investigations show that interleukin-6 has a decisive importance for the pathological mechanisms and acts by means of PGE2 (Wang et al., 1995, J Clin Endocrinol Metab 80: 3553-3560).

The present invention relates to the use of the substances according to the invention for prophylaxis and treatment in the case of ophthalmopathy in connection with Graves' disease or other pathological diseases of the eye.

The natural ligand (agonist) of the EP4 receptor is PGE2, the synthesis of which is mediated by cyclooxygenases (COX) enzymes (COX-1, COX-2). In the aforementioned syndromes, indications and their genesis, these enzymes are usually involved via increased expression and activity. Therefore, in the case of all administration possibilities mentioned, it is possible to combine a COX inhibitor (COX-2 and/or COX-1), with the aim a) of achieving a higher and more effective pharmacological efficacy than with one class of substance and b) of making possible a lower dose of one of the two or both substance classes, which leads to a reduction of possible side effects and better tolerability.

The present invention therefore also relates to medicaments containing a compound of the general formula (I) in combination with a COX inhibitor for the treatment of diseases (combination preparations). COX inhibitors that may be mentioned are, for example, the non-selective COX inhibitors such as aspirin, naproxen, indomethacin, ibuprofen or the selective COX inhibitors meloxicam, ketoprofen, piroxicam, tenoxicam, nimesulide, mefanemic acid, ketoralac, celecoxib (4-[5-(4-methylphenyl)-3-(trifluoromethyl)-1H-pyrazol-1-yl]benzenesulphonamide), parecoxib (N-[4-(5-methyl-3-phenyl-4-isoxazolyl)phenyl]-sulphonyl-propionamide), rofecoxib (4-(4-mesylphenyl)-3-phenyl-furan-2(5H)-one), valdecoxib (4-[5-methyl-3-phenyl-4-isoxazoyl]benzenesulphonamide), NS-398 (N-methyl-2-cyclohexanoxy-4-nitrobenzenesulphonamide), lumiracoxib [2-(2'-chloro-6'-fluorophenyl)-amino-5-methylbenzeneacetic acid], ceracoxib and etoricoxib.

These combination preparations can be employed for the treatment of the following diseases: infectious disorders, cancer, cardiovascular disorders, angiogenetic disorders, impaired uterine contractions, pain, inflammatory disorders, neuroinflammatory disorders, neurodegenerative disorders, autoimmune disorders, immune-dependent disorders/therapies, nephrological disorders, ophthalmological disorders.

The alternative reaction schemes according to which the compounds according to the invention can be prepared, in each case depending on the availability of the starting materials, are shown below. For all schemes, working examples illustrate the practice of the reaction in detail.

The radicals R, $R^{1a}$, $R^{1b}$, $R^4$, $R^5$, $R^{5'}$, $R^6$, $R^7$, $R^8$, $R^9$, $R^{10}$, A and B shown in Schemes 1-7 have the meanings given in the claim and serve to illustrate the synthesis, without the scope of the compounds claimed being limited to these examples.

Thus, for example, by reacting substituted o-phenylenediamines of the general formula II or XI with aldehydes of the formula III, XXIV or XXI, it is possible to prepare benzimidazoles of the general structure IV or XII. This can be achieved, for example, by heating the components II and III in the presence of acids and an oxidizing agent. The compounds IV and XII generated in this manner can then be substituted at the nitrogen atoms of the imidazole using a method known from the literature, preferably with alkyl halides, oxiranes or other nucleophiles (Scheme 1, Scheme 3). In this synthesis variant, the isomers Va and Vb or else XIIa and XIIb, which can be separated by customary methods, are generally formed. Customary methods are separation processes such as, for example, crystallization, chromatography on silica gel or else separations by high pressure or high performance liquid chromatography.

Carboxylic acids of the formula VI can be reacted with an amine by the processes known to the person skilled in the art to give the compounds of the general formula I according to the invention (Schemes 1-4, general formula VII).

Conversion into amides of the formula VII takes place, for example, by transforming a carboxylic acid of the formula VI in the presence of a tertiary amine, for example triethylamine, with isobutyl chloroformate into a mixed anhydride which reacts with an alkali metal salt of the corresponding amine in an inert solvent or solvent mixture, for example tetrahydrofuran, N,N-dimethylformamide, dimethoxyethane at temperatures between −30° C. and +60° C. to give the target compounds of the formula I.

It is also possible to activate a carboxylic acid VI with reagents such as, for example, dicyclohexylcarbodiimide (DCC), 1-(3-dimethylaminopropyl)-3-ethylcarbodiimide (EDCI), N-hydroxybenzotriazole (HOBT), N-[(dimethylamino)-(3H-[1,2,3]triazolo[4,5-b]pyridin-3-yloxy)methylidene]-N-methylmethanaminium hexafluorophosphate (HATU). For example, the reaction with HATU is carried out in an inert solvent, for example N,N-dimethylformamide, dimethyl sulphoxide in the presence of the appropriate amine and a tertiary amine, for example triethylamine, diisopropylethylamine, at temperatures between −30° C. and +60° C.

It is also possible to convert a carboxylic acid of the formula VI with an inorganic acid chloride, for example phosphorus pentachloride, phosphorus trichloride, thionyl chloride into the corresponding carbonyl chloride, and then in pyridine or an inert solvent such as, for example, N,N-dimethylformamide in the presence of the appropriate amine and a tertiary amine, for example triethylamine, at temperatures between −30° C. and +60° C. into the target compounds of the general formula I.

The compounds of the general formula I according to the invention can also be obtained from amines of the general formula XXXII by reaction with carboxylic acids, carbonyl chlorides or carboxylic anhydrides.

The compounds of the general formula I according to the invention can also be obtained from bromoimidazoles of the general formula XIII (XIIIa and/or XIIIb) under palladium (0) catalysis by reaction with an appropriate alcohol or amine and carbon monoxide (CO) or a carbon monoxide source such as, for example, molybdenum hexacarbonyl in a suitable solvent or solvent mixture, for example 1,4-dioxane/water or tetrahydrofuran, addition of a base such as, for example, sodium carbonate or 1,8-diazabicyclo(5.4.0)undec-7-ene (DBU) and a catalyst/ligand mixture, for example palladium(II) acetate or trans-bis(acetato)bis[o-(di-o-tolylphosphino)benzyl]dipalladium(II)/tri-tert-butylphosphino tetrafluoroborate at temperatures between 80° C. and 160° C. (if appropriate with microwave irradiation between 80-200 Watt), and in the case that carbon monoxide is used at a CO pressure of 5-15 bar (Scheme 3, Scheme 4). This method is not limited to methyl esters, i.e. to the use of methanol, but can also be extended to other esters. Thus, for example, by using ethanol instead of methanol it is possible to synthesize the corresponding ethyl esters in this manner.

The carboxylic acids of the general formula VI can be obtained, for example, from esters of the formula Va by ester hydrolysis in a suitable solvent or solvent mixture, for example methanol, ethanol, tetrahydrofuran, water, with addition of an aqueous solution of an alkali metal hydroxide, for example sodium hydroxide, lithium hydroxide, at temperatures between 20° C. and 60° C. (Schemes 1-4).

The compounds of the general formula XXIV can be prepared, for example, from the corresponding anilines XX by cyclizing XX by methods known to the person skilled in the art to give formula XXII and then oxidizing to give XXIII. The compounds XXIII generated in this manner can be alkylated at the nitrogen of the carbazole by methods known from the literature (Scheme 5) and then be used in reactions in which the benzimidazoles of the formula I according to the invention are prepared.

Scheme 1

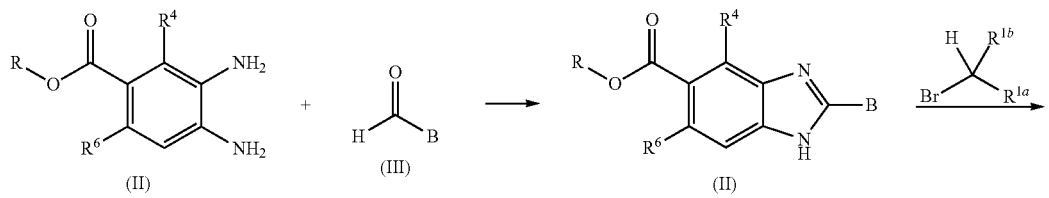

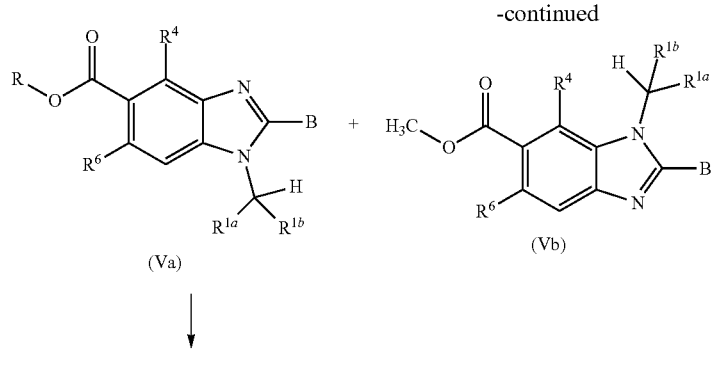
(Va)      (Vb)
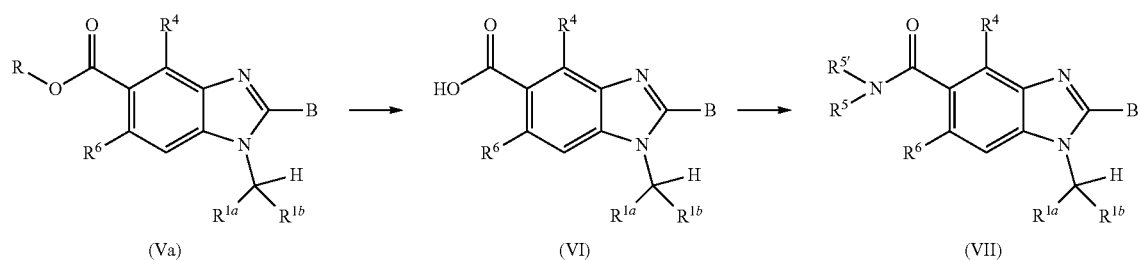
(Va)      (VI)      (VII)
Scheme 2
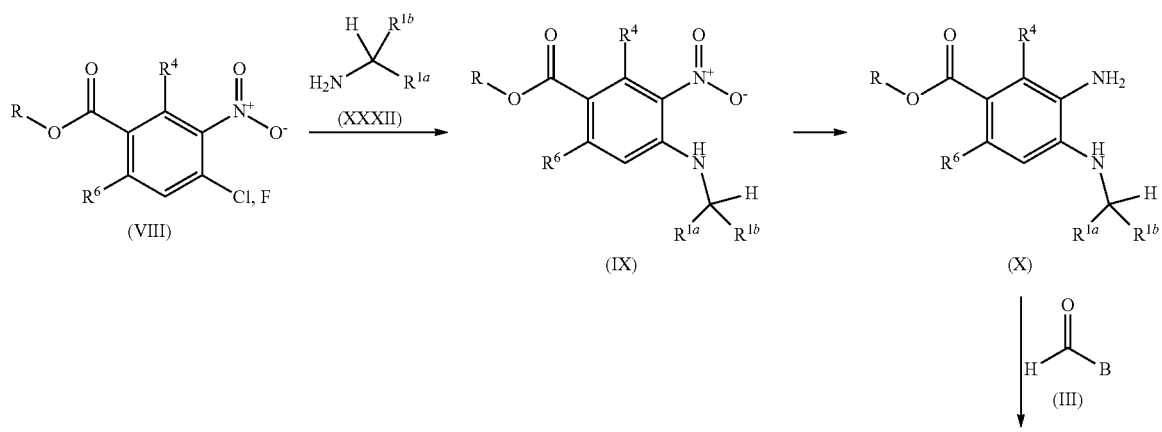
(VIII)      (IX)      (X)
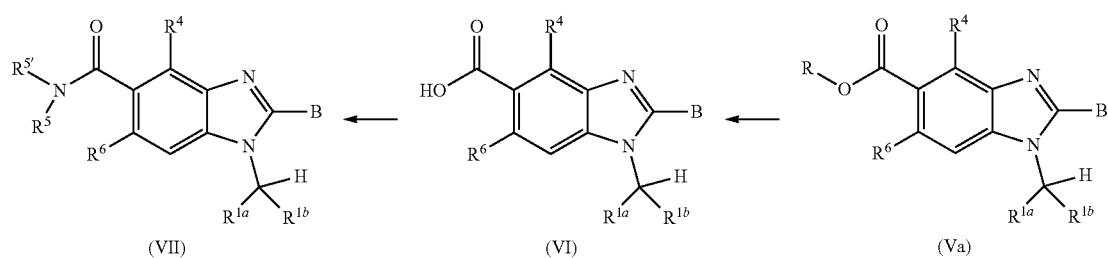
(VII)      (VI)      (Va)

Scheme 3
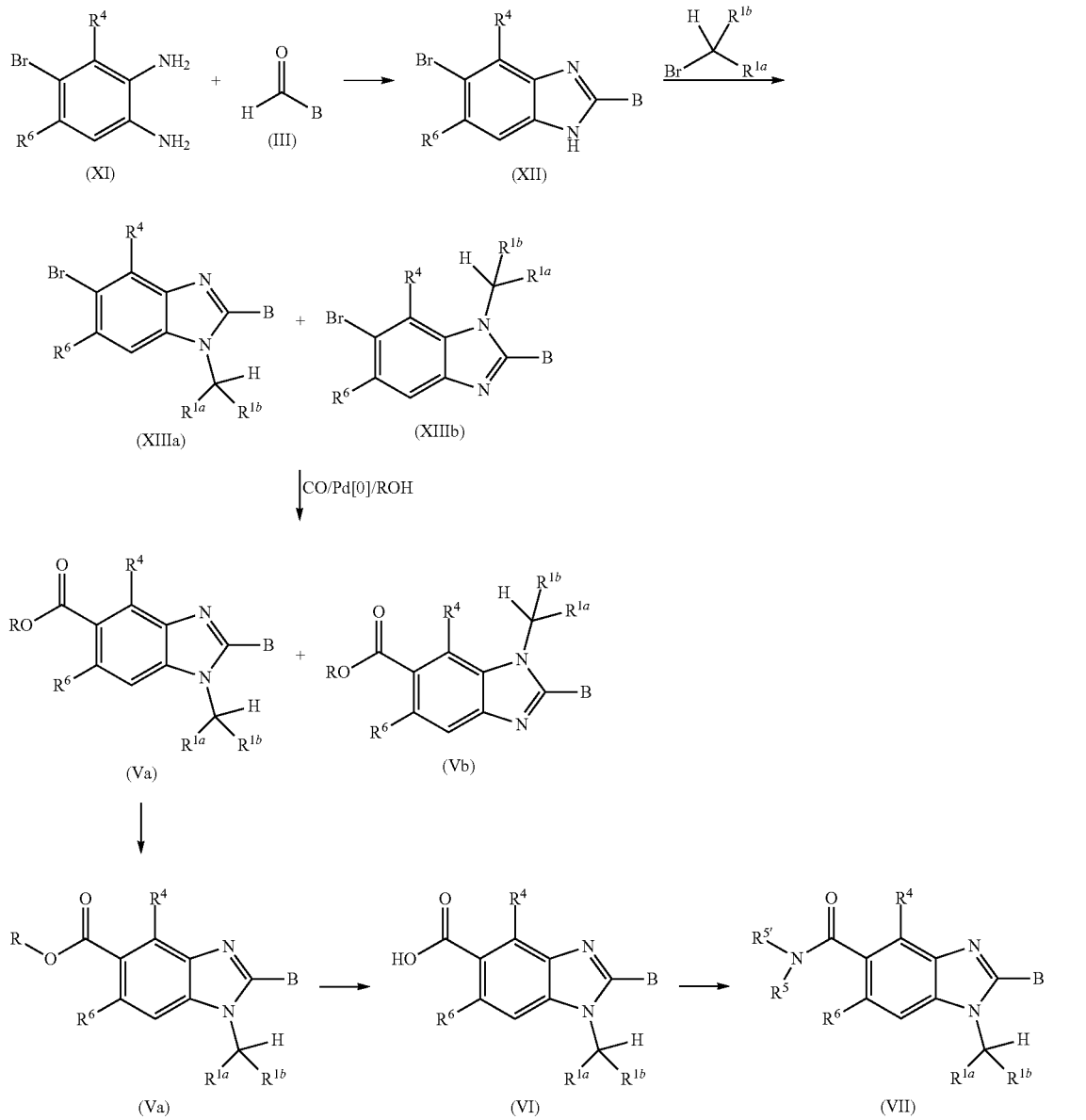
Scheme 4
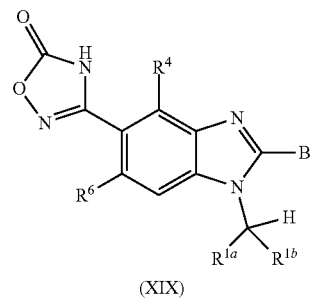

-continued
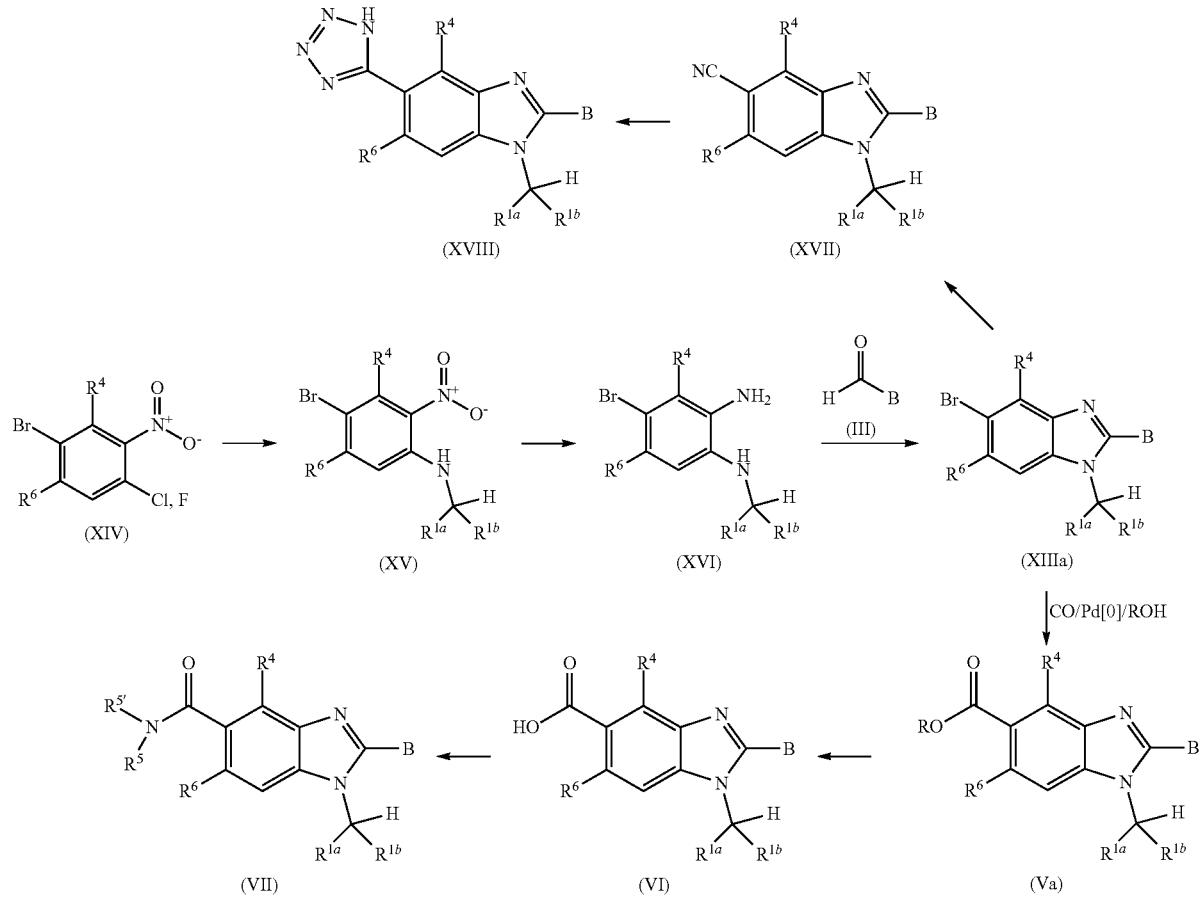
Scheme 5
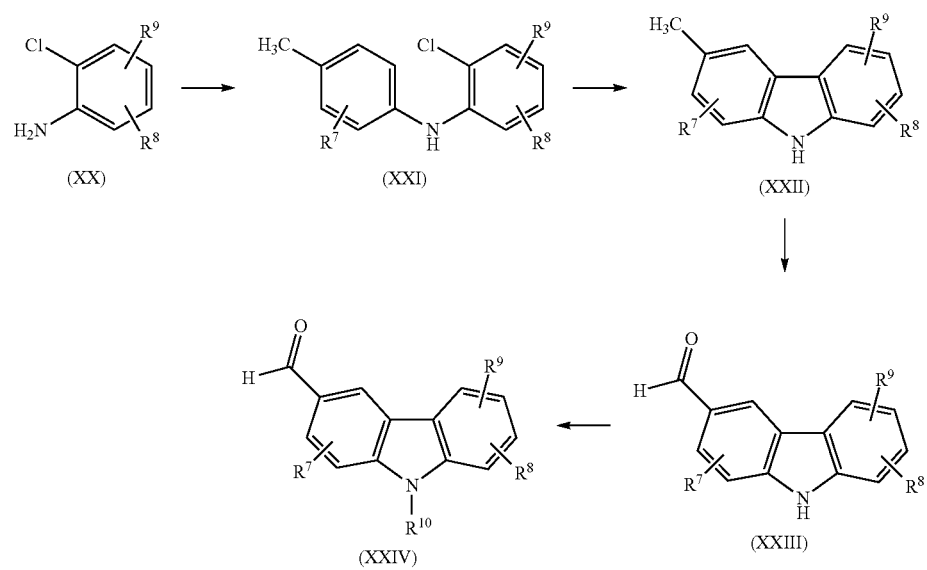

Scheme 6

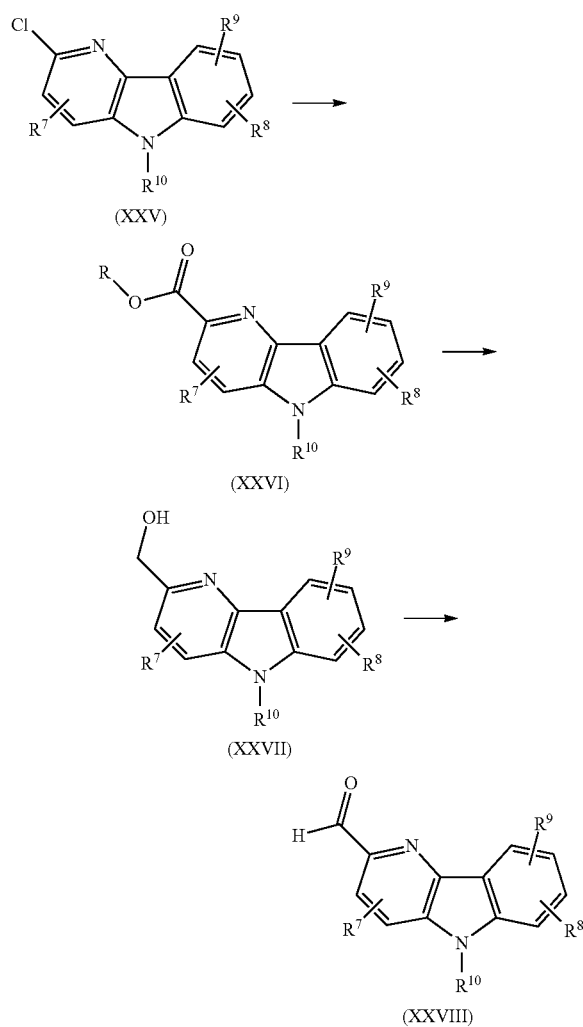

Scheme 7

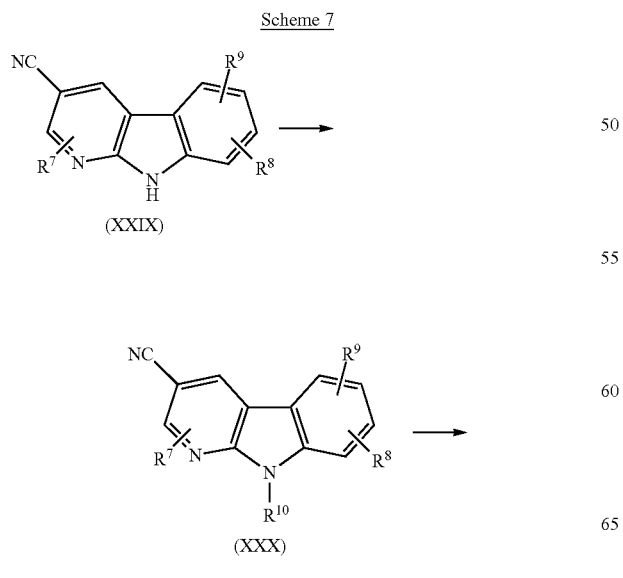

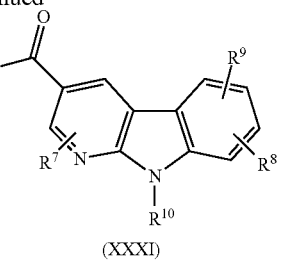

(XXXI)

Preparation of the Compounds According to the Invention

The examples which follow illustrate the preparation of the compounds of the general formula (I) according to the invention without limiting the scope of the compounds claimed to these examples.

The compounds of the general formula (I) according to the invention can be prepared and characterized as described below.

ABBREVIATIONS

DCM dichloromethane
DMF N,N-dimethylformamide
DMSO dimethyl sulphoxide
h hour(s)
HPLC high-pressure high-performance liquid chromatography
M molar
min minute(s)
N normal
NMR nuclear magnetic resonance spectroscopy
RT room temperature
THF tetrahydrofuran MNR peak forms are stated as they appear in the spectrum, possible higher order effects were disregarded.

EXPERIMENTAL PART

Intermediate 1

Ethyl 4-[(2-methoxyethyl)amino]-3-nitrobenzoate

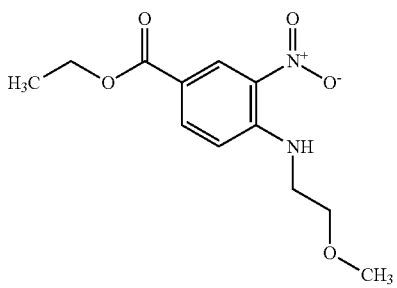 [SMILES: CCOC(=O)c1ccc(NCCOC)c([N+](=O)[O-])c1]

40.0 g (0.17 mol) of ethyl 4-chloro-3-nitrobenzoate were added to 200 ml of DMSO, 20.9 g (0.28 mol) of 2-methoxyethanamine were added, the mixture was heated at 60° C. for 6 h and then cooled to RT overnight. The reaction mixture was poured onto 200 ml of saturated sodium bicarbonate solution and the resulting precipitate was filtered off and washed with 100 ml of water. The precipitate was dried. This gave 45.5 g (78%) of the title compound.

¹H-NMR (300 MHz, DMSO-d6), δ [ppm]=1.31 (t, 3H), 3.31-3.32 (m, 1H), 3.57-3.62 (m, 4H), 4.29 (q, 2H), 7.19 (d, 1H), 7.97 (dd, 1H), 8.50-8.56 (m, 1H), 8.61 (d, 1H).

Intermediate 2

4-[(2-Methoxyethyl)amino]-3-nitrobenzoic Acid

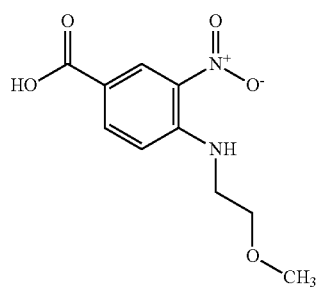 [SMILES: COCCNc1ccc(C(=O)O)cc1[N+](=O)[O-]]

26.0 g (0.097 mol) of ethyl 4-[(2-methoxyethyl)amino]-3-nitrobenzoate were added to 100 ml of ethanol, 55 ml of 2M aqueous sodium hydroxide solution were added and the mixture was heated at reflux for 1 h. After cooling, 75 mol of 2M hydrochloric acid were added and the mixture was extracted five times with dichloromethane. The combined organic phases were dried over sodium sulphate, filtered and concentrated. This gave 21.8 g (93%) of the title compound.

¹H-NMR (300 MHz, DMSO-d6), δ [ppm]=3.31 (s, 3H), 3.57-3.61 (4H), 7.17 (d, 1H), 7.96 (dd, 1H), 8.47-8.53 (br. s., 1H), 8.61 (d, 1H), 12.40-13.30 (1H).

Intermediate 3

3-Amino-4-[(2-methoxyethyl)amino]benzoic Acid

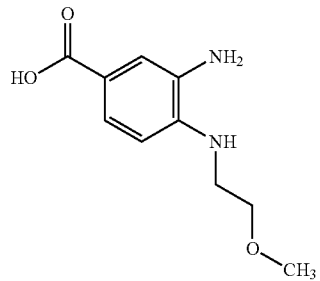

21.8 g (0.09 mol) of 4-[(2-methoxyethyl)amino]-3-nitrobenzoic acid were dissolved in 500 ml of ethanol, 2.5 g of palladium/carbon (10%) were added and the mixture was stirred at RT with introduction of hydrogen for 4 h. Another 2.5 g of palladium/carbon (10%) were added, and hydrogen was introduced for a further 2 h. The catalyst was filtered off and the solution was concentrated. This gave 19.0 g (82%) of the title compound.

¹H-NMR (400 MHz, DMSO-d6), δ [ppm]=3.23-3.31 (m, 5H), 3.41-3.48 (m, 2H), 5.35-5.65 (1H), 5.70-6.20 (2H), 6.15 (d, 1H), 6.70 (s, 1H), 7.16 (d, 1H), 11.40-12.50 (1H).

Intermediate 4

Ethyl 3-amino-4-[(2-methoxyethyl)amino]benzoate

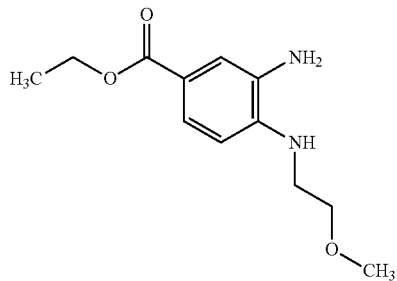 [SMILES: CCOC(=O)c1ccc(NCCOC)c(N)c1]

Ethyl 3-amino-4-[(2-methoxyethyl)amino]benzoate was prepared analogously to Intermediate 3 from ethyl 4-[(2-methoxyethyl)amino]-3-nitrobenzoate by reduction with hydrogen over palladium.

¹H-NMR (400 MHz, DMSO-d6), δ [ppm]=1.25 (t, 3H), 3.25-3.31 (m, 5H), 3.42-3.47 (m, 2H), 4.13-4.20 (m, 2H), 6.02 (br. s., 1H), 6.17 (d, 1H), 6.71 (d, 1H), 7.18 (dd, 1H), NH2 not stated.

Intermediate 5

Methyl 3-amino-2-fluoro-4-[(2-methoxyethyl)amino]benzoate

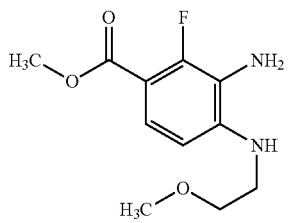 [SMILES: COCCNc1ccc(C(=O)OC)c(F)c1N]

Under nitrogen and at −78° C., a solution of 16.0 g (0.21 mol) of 2-methoxyethanol in 315 ml of DCM was added dropwise over a period of 20 min to 29.4 g (0.23 mol) of oxalyl chloride in 315 ml of DCM, the mixture was stirred for 1 h, 88 ml (0.63 mol) of triethylamine were added dropwise with continued cooling and cooling was then removed. After warming to RT, the reaction mixture obtained in this manner was added to a solution of 9.5 g (40.4 mmol) of 4-bromo-3-fluoro-2-nitroaniline in 50 ml of DCM, 60 g (0.28 mol) of sodium triacetoxyborohydride and, slowly, 62 ml (0.81 mol) of trifluoroacetic acid were added in succession and the reaction mixture was then stirred at RT for 17 h. The mixture was then filtered, 0.5 l of ammonia solution (33% strength) was slowly added to the filtrate, the mixture was extracted repeatedly with DCM, the combined organic phases were evaporated to dryness and the residue was purified on silica gel (13.7 g).

13.7 g of the crude product obtained were dissolved in 500 ml of methanol, 7.6 g (9.3 mmol) of 1,1-bis(diphenylphosphino)ferrocenepalladium(II) dichloride and 18.4 g (0.19 mol) of potassium acetate were added and the mixture was stirred under carbon monoxide at 13 bar and 100° C. in an autoclave for 19 h. After cooling to RT, the mixture was filtered, the filtrate was concentrated under reduced pressure and the resulting crude methyl 3-amino-2-fluoro-4-[(2-methoxyethyl)amino]benzoate (9.0 g, 92%) was used for the next step without further purification.

¹H-NMR (400 MHz, DMSO-d6), δ [ppm]=3.28 (s, 3H), 3.29-3.22 (m, 2H), 3.50-3.54 (m, 2H), 3.73 (s, 3H), 4.64 (s, 2H), 5.59 (t, 1H), 6.34 (d, 1H), 7.11 (t, 1H).

Intermediates 6 and 7

8-Chloro-9-ethyl-6-methyl-9H-carbazole-3-carbaldehyde and 5-chloro-9-ethyl-6-methyl-9H-carbazole-3-carbaldehyde

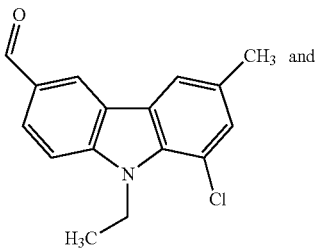

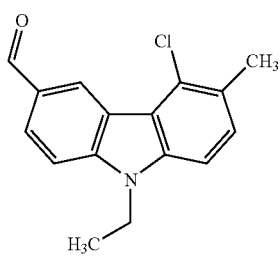

2.0 g (8.43 mmol) of 9-ethyl-6-methyl-9H-carbazole-3-carbaldehyde and 1.1 g (9.27 mmol) of N-chlorosuccinimide (NCS) were added to 29 ml of acetonitrile, and the mixture was stirred at 60° C. for 3 h. The reaction mixture was then taken up in ethyl acetate, the organic phase was washed with water and the residue obtained after evaporation was purified chromatographically on silica gel (hexane/ethyl acetate 9:1->7:3). This gave 1.2 g (52%) of 8-chloro-9-ethyl-6-methyl-9H-carbazole-3-carbaldehyde and 0.7 g (31%) of 5-chloro-9-ethyl-6-methyl-9H-carbazole-3-carbaldehyde.

8-Chloro-9-ethyl-6-methyl-9H-carbazole-3-carbaldehyde

¹H-NMR (400 MHz, DMSO-d6), δ [ppm]=1.37 (t, 3H), 2.47 (s, 3H), 4.78 (q, 2H), 7.38 (s, 1H), 7.79 (d, 1H), 7.98-8.03 (m, 1H), 8.07 (s, 1H), 8.71 (s, 1H), 10.05 (s, 1H).

5-Chloro-9-ethyl-6-methyl-9H-carbazole-3-carbaldehyde

¹H-NMR (400 MHz, DMSO-d6), δ [ppm]=1.32 (t, 3H), 4.51 (q, 2H), 7.51 (d, 1H), 7.63 (d, 1H), 7.81 (d, 1H), 8.03 (dd, 1H), 9.01 (d, 1H), 10.08 (s, 1H).

Intermediate 8

Methyl 3-amino-4-[(2-methoxyethyl)amino]-2-methylbenzoate

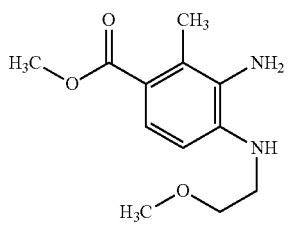

27.5 g (0.12 mol) of a mixture of methyl 4-chloro-2-methyl-5-nitrobenzoate and methyl 4-chloro-2-methyl-3-nitrobenzoate, prepared according to M. Baumgarth et al., J. Med. Chem. 1997, 40, 2017-2034, were added to 50 ml of DMSO, 31 ml (0.36 mol) of 2-methoxyethanamine were added and the mixture was stirred at 80° C. for 25 h. Water was then added, the mixture was extracted repeatedly with DCM and the combined organic phases were evaporated. The residue was separated chromatographically on silica gel (hexane/DCM 1:0→0:1). This gave 9.3 g (29%) of methyl 4-[(2-methoxyethyl)amino]-2-methyl-3-nitrobenzoate and 15.5 g (49%) of methyl 4-[(2-methoxyethyl)amino]-2-methyl-5-nitrobenzoate.

Methyl 4-[(2-methoxyethyl)amino]-2-methyl-3-nitrobenzoate

¹H-NMR (400 MHz, DMSO-d6), δ [ppm]=2.37 (s, 3H), 3.26 (s, 3H), 3.36 (q, 2H), 3.47 (t, 2H), 3.77 (s, 3H), 6.42 (t, 1H), 6.86 (d, 1H), 7.83 (d, 1H).

Methyl 4-[(2-methoxyethyl)amino]-2-methyl-5-nitrobenzoate

¹H-NMR (400 MHz, DMSO-d6), δ [ppm]=2.55 (s, 3H), 3.32 (s, 3H), 3.56-3.62 (m, 4H), 3.79 (s, 3H), 6.99 (s, 1H), 8.39-8.44 (m, 1H), 8.64 (s, 1H).

3.33 g (12.4 mmol) of methyl 4-[(2-methoxyethyl) amino]-2-methyl-3-nitrobenzoate were dissolved in 80 ml of THF/methanol (1:1) and hydrogenated under standard pressure over palladium (10% on carbon). The catalyst was filtered off and the filtrate was concentrated. This gave 2.85 g (92%) of crude methyl 3-amino-4-[(2-methoxyethyl) amino]-2-methylbenzoate which was used without further purification for the following steps.

¹H-NMR (400 MHz, DMSO-d6), δ [ppm]=2.31 (s, 3H), 3.25-3.31 (m, 5H), 3.53 (t, 2H), 3.70 (s, 3H), 4.44 (br, 2H), 5.20 (t, 1H), 6.37 (d, 1H), 7.18 (d, 1H).

Intermediate 9

9-Ethyl-8-fluoro-6-methyl-9H-carbazole-3-carboxylic Acid

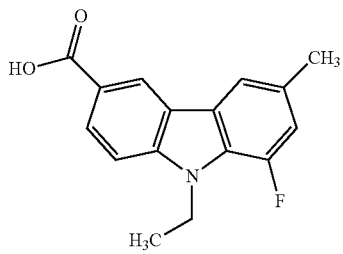 [SMILES: CCn1c2ccc(C(=O)O)cc2c2cc(C)cc(F)c21]

A mixture of 2.49 g (11.8 mmol) of [5-(ethoxycarbonyl)-2-fluorophenyl]boronic acid, 1.60 g (7.8 mmol) of 2-bromo-6-fluoro-4-methylaniline, 0.96 g (1.2 mmol) of 1,1'-bis(diphenylphosphino)ferrocenedichloropalladium(II) and 2.60 g (18.8 mmol) of potassium carbonate in 79 ml of tetrahydrofuran was heated at reflux for 3 h, water was added after cooling and the mixture was then extracted with ethyl acetate. The combined organic phases were washed with water until neutral, dried with sodium sulphate and evaporated to dryness, and the residue was purified on silica gel. The resulting crude ethyl 2'-amino-3',6-difluoro-5'-methylbiphenyl-3-carboxylate was used as such for the next step.

557 mg (1.91 mmol) of crude ethyl 2'-amino-3',6-difluoro-5'-methylbiphenyl-3-carboxylate were added to 17 ml of DMF, 268 mg (6.69 mmol) of sodium hydride (60% strength dispersion in mineral oil) were added and the mixture was heated in a pressure tube at 90° C. for 90 h. After cooling, the mixture was carefully poured onto ice-water and extracted with DCM. The aqueous phase was acidified to pH 4, re-extracted with DCM and then, together with the organic phase initially obtained, dried with sodium sulphate and evaporated to dryness. This gave a crude mixture (419 mg) of ethyl 8-fluoro-6-methyl-9H-carbazole-3-carboxylate and 8-fluoro-6-methyl-9H-carbazole-3-carboxylic acid which was used directly for the next step.

419 mg of a mixture of ethyl 8-fluoro-6-methyl-9H-carbazole-3-carboxylate and 8-fluoro-6-methyl-9H-carbazole-3-carboxylic acid were added to 23 ml of acetone, 2.8 g (8.6 mmol) of caesium carbonate and 1.0 ml (12.9 mmol) of ethyl iodide were added and the mixture was heated at 45° C. for 24 h. After cooling, the mixture was filtered, the filter residue was washed with acetone and ethyl acetate and the filtrate was evaporated to dryness. The residue was taken up in 1.5 ml of ethanol, 2 ml of 2 N aqueous sodium hydroxide solution were added and the mixture was heated at 45° C. for 5 h. The mixture was then acidified to pH 2 using 1 M hydrochloric acid, extracted with ethyl acetate, dried with sodium sulphate and subsequently evaporated to dryness. This gave 435 mg (14%, 4 steps) of 9-ethyl-8-fluoro-6-methyl-9H-carbazole-3-carboxylic acid.

$^1$H-NMR (400 MHz, DMSO-d6), δ [ppm]=1.35 (t, 3H), 2.47 (s, 3H), 4.53 (q, 2H), 7.17 (d, 1H), 7.69 (d, 1H), 7.91 (s, 1H), 8.07 (dd, 1H), 8.74 (d, 1H), 12.61 (s, 1H).

Intermediate 10

9-Ethyl-6-fluoro-8-methyl-9H-carbazole-3-carboxylic Acid

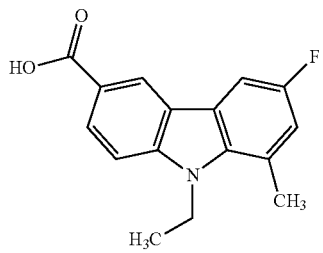 [SMILES: CCn1c2ccc(C(=O)O)cc2c2cc(F)cc(C)c21]

9-Ethyl-6-fluoro-8-methyl-9H-carbazole-3-carboxylic acid was prepared analogously to the synthesis described for Intermediate 35 for 9-ethyl-8-fluoro-6-methyl-9H-carbazole-3-carboxylic acid from 2.75 (13.5 mmol) of 2-bromo-4-fluoro-6-methylaniline and 2.6 g (12.3 mmol) of [5-(ethoxycarbonyl)-2-fluorophenyl]boronic acid over 4 steps (543 mg, 20%).

$^1$H-NMR (400 MHz, DMSO-d6), δ [ppm]=1.33 (t, 3H), 2.79 (s, 3H), 4.63 (q, 2H), 7.15 (dd, 1H), 7.67 (d, 1H), 7.99 (dd, 1H), 8.05 (dd, 1H), 8.78 (d, 1H), 12.59 (br. s., 1H).

Example 1

Methyl 2-(6-bromo-9-ethyl-9H-carbazol-3-yl)-1-(2-methoxyethyl)-4-methyl-1H-benzimidazole-5-carboxylate

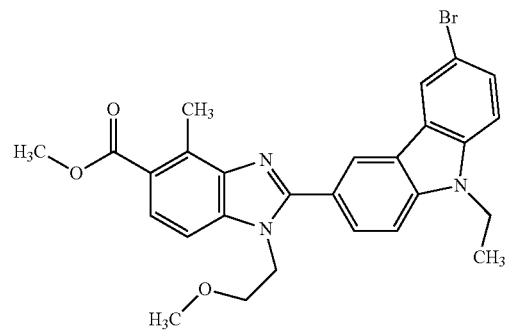 [SMILES: CCn1c2ccc(Br)cc2c2cc(-c3nc4c(C)c(C(=O)OC)ccc4n3CCOC)ccc21]

180 mg (0.94 mmol) of sodium disulphite were added to 0.9 ml of water, and 100 mg (0.4 mmol) of methyl 3-amino-4-[(2-methoxyethyl)amino]-2-methylbenzoate (Intermediate 8) and 127 mg (0.4 mmol) of 6-bromo-9-ethyl-9H-carbazole-3-carbaldehyde were then added, followed by 1.3 ml of THF. The mixture was first stirred at room temperature and then heated at reflux for 1 h. After cooling, the reaction mixture was concentrated and the residue obtained after evaporation was purified chromatographically. This gave 139 mg (63%) of methyl 2-(6-bromo-9-ethyl-9H-carbazol-3-yl)-1-(2-methoxyethyl)-4-methyl-1H-benzimidazole-5-carboxylate as a solid.

$^1$H-NMR (400 MHz, DMSO-d6), δ [ppm]=1.36 (t, 3H), 2.89 (s, 3H), 3.09 (s, 3H), 3.66 (t, 2H), 3.87 (s, 3H), 4.48-4.61 (m, 4H), 7.59-7.72 (m, 3H), 7.80-7.86 (m, 2H), 7.97 (dd, 1H), 8.55 (d, 1H), 8.69 (d, 1H).

Example 2

2-(6-Bromo-9-ethyl-9H-carbazol-3-yl)-1-(2-methoxyethyl)-4-methyl-1H-benzimidazole-5-carboxylic Acid

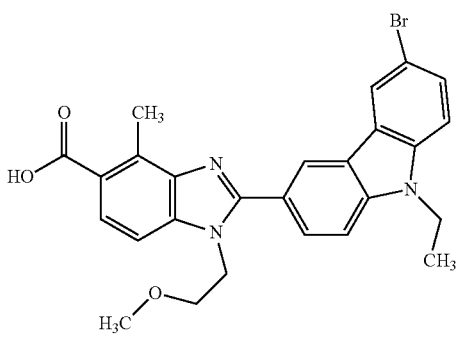 [SMILES: CCn1c2ccc(Br)cc2c2cc(-c3nc4c(C)c(C(=O)O)ccc4n3CCOC)ccc21]

130 mg (0.25 mmol) of methyl 2-(6-bromo-9-ethyl-9H-carbazol-3-yl)-1-(2-methoxyethyl)-4-methyl-1H-benzimidazole-5-carboxylate were added to a mixture of 2 ml of methanol and 2 ml of THF, 2 ml of 2.0 M aqueous sodium hydroxide solution were added and the mixture was heated at reflux for 8 h. After cooling to RT, the mixture was extracted three times with ethyl acetate and the organic phases were discarded. The resulting aqueous phase was acidified to pH 3 using 2 M hydrochloric acid and extracted repeatedly with ethyl acetate, and the organic phases obtained in this manner were concentrated to dryness. This gave 96 mg (74%) of the title compound.

$^1$H-NMR (400 MHz, DMSO-d6), δ [ppm]=1.36 (t, 3H), 2.89 (s, 3H), 3.10 (s, 3H), 3.67 (t, 2H), 4.48-4.59 (m, 4H), 7.55 (d, 1H), 7.64 (dd, 1H), 7.69 (d, 1H), 7.79-7.86 (m, 2H), 7.96 (dd, 1H), 8.54 (d, 1H), 8.69 (d, 1H), 12.20-13.00 (br., 1H).

Example 3

Methyl 2-(9-ethyl-8-fluoro-6-methyl-9H-carbazol-3-yl)-1-(2-methoxyethyl)-4-methyl-1H-benzimidazole-5-carboxylate

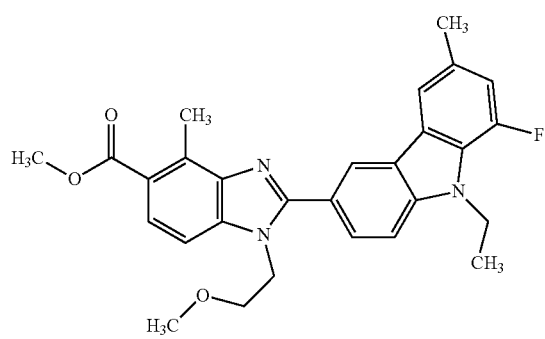 [SMILES: CCn1c2ccc(-c3nc4c(C)c(C(=O)OC)ccc4n3CCOC)cc2c2cc(C)cc(F)c21]

A mixture of 100 mg (0.42 mmol) of methyl 3-amino-4-[(2-methoxyethyl)amino]-2-methylbenzoate (Intermediate 8), 114 mg (0.42 mmol) of 9-ethyl-8-fluoro-6-methyl-9H-carbazole-3-carboxylic acid (Intermediate 9) and 1.25 ml (2.1 mmol) of propanephosphonic anhydride solution (50% in DMF) in 2 ml of pyridine were heated in a pressure tube at 100° C. for 90 h. After cooling, the mixture was poured onto water and extracted repeatedly with ethyl acetate, the combined organic phases were dried with sodium sulphate and evaporated to dryness and the residue was purified by preparative HPLC. This gave 60 mg (30%) of methyl 2-(9-ethyl-8-fluoro-6-methyl-9H-carbazol-3-yl)-1-(2-methoxyethyl)-4-methyl-1H-benzimidazole-5-carboxylate.

$^1$H-NMR (300 MHz, DMSO-d6): δ [ppm]=1.39 (t, 3H), 2.49 (s, 3H), 2.88 (s, 3H), 3.11 (s, 3H), 3.68 (t, 2H), 3.87 (s, 3H), 4.53-4.61 (m, 4H), 7.21 (d, 1H), 7.62 (d, 1H), 7.80-7.87 (m, 2H), 7.91-7.99 (m, 2H), 8.63 (d, 1H).

Example 4

2-(9-Ethyl-8-fluoro-6-methyl-9H-carbazol-3-yl)-1-(2-methoxyethyl)-4-methyl-1H-benzimidazole-5-carboxylic Acid

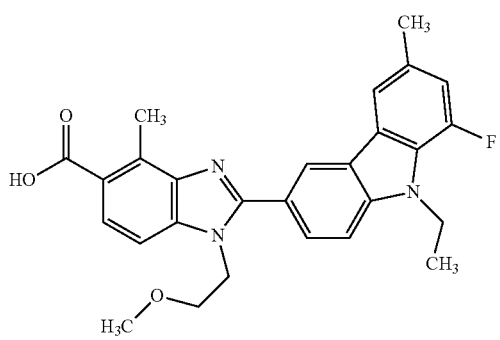 [SMILES: CCn1c2ccc(-c3nc4c(C)c(C(=O)O)ccc4n3CCOC)cc2c2cc(C)cc(F)c21]

60 mg (0.13 mmol) of methyl 2-(9-ethyl-8-fluoro-6-methyl-9H-carbazol-3-yl)-1-(2-methoxyethyl)-4-methyl-1H-benzimidazole-5-carboxylate were taken up in 10 ml of methanol, 0.32 ml (0.63 mmol) of 2 M aqueous sodium hydroxide solution were added and the mixture was heated at 60° C. for 17 h. After cooling, the mixture was evaporated, the residue was adjusted to pH 3 using 2 M hydrochloric acid and extracted repeatedly with ethyl acetate and the combined organic phases were evaporated and purified on silica gel. This gave 40 mg (69%) of the title compound.

$^1$H-NMR (400 MHz, DMSO-d6), δ [ppm]=1.39 (t, 3H), 2.49 (s, 3H), 2.89 (s, 3H), 3.12 (s, 3H) 3.69 (t, 2H), 4.52-4.64 (m, 4H), 7.20 (d, 1H), 7.60 (d, 1H), 7.81-7.99 (m, 4H), 8.63 (d, 1H), 12.40-12.75 (br., 1H).

Example 5

Methyl 2-(9-ethyl-6-fluoro-8-methyl-9H-carbazol-3-yl)-1-(2-methoxyethyl)-4-methyl-1H-benzimidazole-5-carboxylate

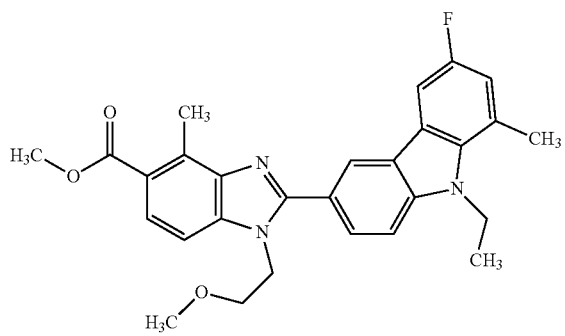

Analogously to Example 3, 100 mg (0.42 mmol) of methyl 3-amino-4-[(2-methoxyethyl)amino]-2-methylbenzoate (Intermediate 8) and 114 mg (0.42 mmol) of 9-ethyl-6-fluoro-8-methyl-9H-carbazole-3-carboxylic acid (Intermediate 10) gave methyl 2-(9-ethyl-6-fluoro-8-methyl-9H-carbazol-3-yl)-1-(2-methoxyethyl)-4-methyl-1H-benzimidazole-5-carboxylate.

¹H-NMR (400 MHz, DMSO-d6), δ [ppm]=1.38 (t, 3H), 2.84 (s, 3H), 2.90 (s, 3H), 3.11 (s, 3H), 3.74 (t, 2H), 3.91 (s, 3H), 4.66-4.75 (m, 4H), 7.23 (dd, 1H), 7.90-8.07 (m, 5H), 8.78 (d, 1H).

Example 6

2-(9-Ethyl-6-fluoro-8-methyl-9H-carbazol-3-yl)-1-(2-methoxyethyl)-4-methyl-1H-benzimidazole-5-carboxylic Acid

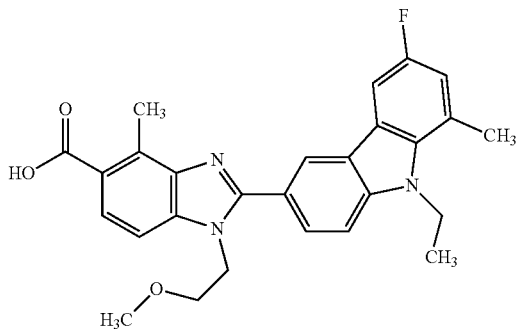 [SMILES: CCn1c2ccc(-c3nc4c(C)c(C(=O)O)ccc4n3CCOC)cc2c2cc(F)cc(C)c21]

Analogously to Example 4, methyl 2-(9-ethyl-6-fluoro-8-methyl-9H-carbazol-3-yl)-1-(2-methoxyethyl)-4-methyl-1H-benzimidazole-5-carboxylate gave the title compound (38 mg, 20% over 2 steps).

¹H-NMR (400 MHz, DMSO-d6), δ [ppm]=1.37 (t, 3H), 2.83 (s, 3H), 2.89 (s, 3H), 3.10 (s, 3H), 3.67 (t, 2H), 4.54 (t, 2H), 4.68 (q, 2H), 7.17 (dd, 1H), 7.56 (d, 1H), 7.80 (d, 1H), 7.84 (d, 1H), 7.93 (dd, 1H), 7.98 (dd, 1H), 8.61 (d, 1H), 12.00-12.70 (br., 1H).

Example 7

2-(9-Ethyl-6-fluoro-8-methyl-9H-carbazol-3-yl)-4-fluoro-1-(2-methoxyethyl)-1H-benzimidazole-5-carboxylic Acid

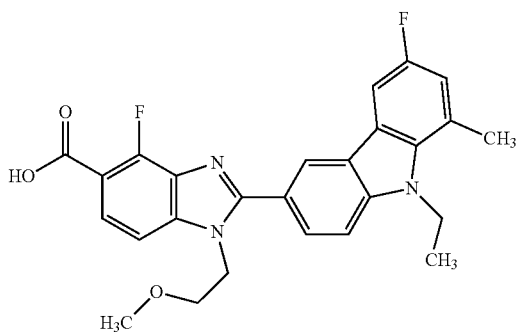 [SMILES: CCn1c2ccc(-c3nc4c(F)c(C(=O)O)ccc4n3CCOC)cc2c2cc(F)cc(C)c21]

Analogously to Example 3, 100 mg (0.41 mmol) of methyl 3-amino-2-fluoro-4-[(2-methoxyethyl)amino]benzoate (Intermediate 5) and 93 mg (0.34 mmol) of 9-ethyl-6-fluoro-8-methyl-9H-carbazole-3-carboxylic acid (Intermediate 10) gave initially methyl 2-(9-ethyl-6-fluoro-8-methyl-9H-carbazol-3-yl)-4-fluoro-1-(2-methoxyethyl)-1H-benzimidazole-5-carboxylate which was then converted analogously to Example 4 into the title compound (6 mg, 3% over 2 steps).

¹H-NMR (400 MHz, DMSO-d6), δ [ppm]=1.37 (t, 3H), 2.83 (s, 3H), 3.12 (s, 3H), 3.69 (t, 2H), 4.56 (t, 2H), 4.68 (q, 2H), 7.17 (dd, 1H), 7.51 (d, 1H), 7.72 (t, 1H), 7.81 (d, 1H), 7.97 (td, 2H), 8.65 (d, 1H), COOH not stated.

Example 8

2-(9-Ethyl-8-fluoro-6-methyl-9H-carbazol-3-yl)-4-fluoro-1-(2-methoxyethyl)-1H-benzimidazole-5-carboxylic Acid

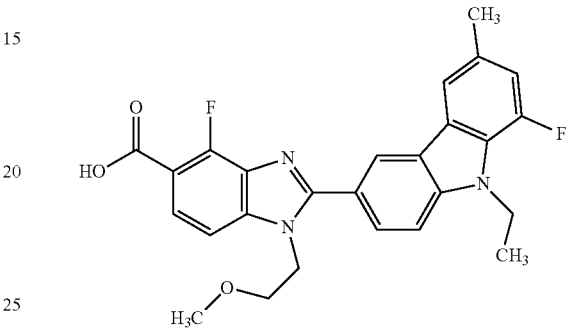

Analogously to Example 3, 100 mg (0.41 mmol) of methyl 3-amino-2-fluoro-4-[(2-methoxyethyl)amino]benzoate (Intermediate 5) and 93 mg (0.34 mmol) of 9-ethyl-8-fluoro-6-methyl-9H-carbazole-3-carboxylic acid (Intermediate 9) gave initially methyl 2-(9-ethyl-8-fluoro-6-methyl-9H-carbazol-3-yl)-4-fluoro-1-(2-methoxyethyl)-1H-benzimidazole-5-carboxylate which was then converted analogously to Example 4 into the title compound (57 mg, 35% over 2 steps).

¹H-NMR (400 MHz, DMSO-d6), δ [ppm]=1.39 (t, 3H), 2.48 (s, 3H), 3.12 (s, 3H), 3.70 (t, 2H), 4.54-4.62 (m, 4H), 7.20 (d, 1H), 7.55 (d, 1H), 7.75 (dd, 1H), 7.83 (d, 1H), 7.92 (s, 1H), 7.97 (dd, 1H), 8.65 (d, 1H), COOH not stated.

Example 9

Ethyl 2-(9-ethyl-8-fluoro-6-methyl-9H-carbazol-3-yl)-1-(2-methoxyethyl)-1H-benzimidazole-5-carboxylate

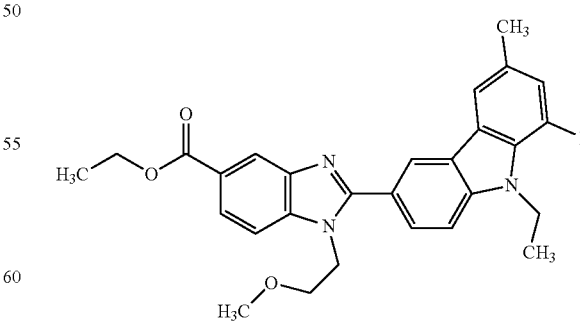

Analogously to Example 3, 100 mg (0.42 mmol) of ethyl 3-amino-4-[(2-methoxyethyl)amino]benzoate (Intermediate 4) and 95 mg (0.35 mmol) of 9-ethyl-8-fluoro-6-methyl-9H-carbazole-3-carboxylic acid (Intermediate 9) gave ethyl 2-(9-ethyl-8-fluoro-6-methyl-9H-carbazol-3-yl)-1-(2-methoxyethyl)-1H-benzimidazole-5-carboxylate (41 mg, 20%).

¹H-NMR (400 MHz, DMSO-d6), δ [ppm]=1.38 (m, 6H), 2.47 (s, 3H), 3.13 (s, 3H), 3.71 (t, 2H), 4.36 (q, 2H), 4.54-4.63 (m, 4H), 7.21 (d, 1H), 7.82 (dd, 2H), 7.89-7.99 (m, 3H), 8.29 (d, 1H), 8.64 (d, 1H).

Example 10

2-(9-Ethyl-8-fluoro-6-methyl-9H-carbazol-3-yl)-1-(2-methoxyethyl)-1H-benzimidazole-5-carboxylic Acid

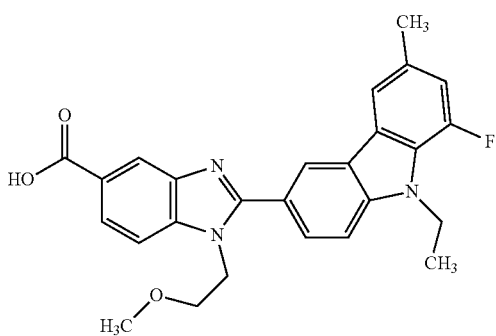 [SMILES: CCn1c2ccc(-c3nc4cc(C(=O)O)ccc4n3CCOC)cc2c2cc(C)cc(F)c21]

Analogously to Example 4, ethyl 2-(9-ethyl-8-fluoro-6-methyl-9H-carbazol-3-yl)-1-(2-methoxyethyl)-1H-benzimidazole-5-carboxylate gave the title compound (23 mg, 59%).

¹H-NMR (400 MHz, DMSO-d6), δ [ppm]=1.39 (t, 3H), 2.47 (s, 3H), 3.13 (s, 3H), 3.72 (t, 2H), 4.53-4.63 (m, 4H), 7.20 (d, 1H), 7.76 (d, 1H), 7.82 (d, 1H), 7.88-8.00 (m, 3H), 8.26 (d, 1H), 8.64 (d, 1H), 12.45-13.05 (br., 1H).

Example 11

Methyl 2-(8-chloro-9-ethyl-6-methyl-9H-carbazol-3-yl)-1-(2-methoxyethyl)-4-methyl-1H-benzimidazole-5-carboxylate

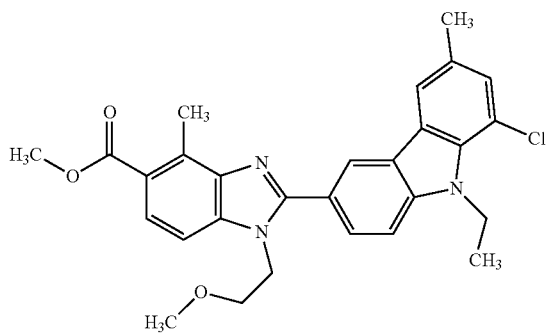 [SMILES: CCn1c2ccc(-c3nc4c(C)c(C(=O)OC)ccc4n3CCOC)cc2c2cc(C)cc(Cl)c21]

Analogously to Example 1, 88 mg (0.37 mmol) of methyl 3-amino-4-[(2-methoxyethyl)amino]-2-methylbenzoate (Intermediate 8) and 100 mg (0.37 mmol) of 8-chloro-9-ethyl-6-methyl-9H-carbazole-3-carbaldehyde (Intermediate 6) gave methyl 2-(8-chloro-9-ethyl-6-methyl-9H-carbazol-3-yl)-1-(2-methoxyethyl)-4-methyl-1H-benzimidazole-5-carboxylate (100 mg, 55%).

¹H-NMR (300 MHz, DMSO-d6), δ [ppm]=1.40 (t, 3H), 2.47 (s, 3H), 2.88 (s, 3H), 3.11 (s, 3H), 3.68 (t, 2H), 3.87 (s, 3H), 4.56 (t, 2H), 4.82 (q, 2H), 7.39 (s, 1H), 7.60 (d, 1H), 7.81-7.86 (m, 2H), 7.97 (dd, 1H), 8.09 (s, 1H), 8.63 (d, 1H).

Example 12

2-(8-Chloro-9-ethyl-6-methyl-9H-carbazol-3-yl)-1-(2-methoxyethyl)-4-methyl-1H-benzimidazole-5-carboxylic Acid

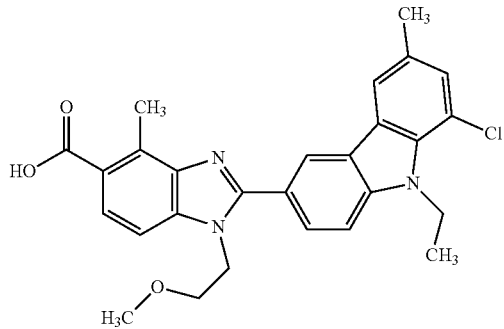 [SMILES: CCn1c2ccc(-c3nc4c(C)c(C(=O)O)ccc4n3CCOC)cc2c2cc(C)cc(Cl)c21]

Analogously to Example 2, methyl 2-(8-chloro-9-ethyl-6-methyl-9H-carbazol-3-yl)-1-(2-methoxyethyl)-4-methyl-1H-benzimidazole-5-carboxylate gave the title compound (60 mg, 61%).

¹H-NMR (300 MHz, DMSO-d6), δ [ppm]=1.40 (t, 3H), 2.47 (s, 3H), 2.89 (s, 3H), 3.11 (s, 3H), 3.68 (t, 2H), 4.55 (t, 2H), 4.82 (q, 2H), 7.39 (s, 1H), 7.57 (d, 1H), 7.80-7.88 (m, 2H), 7.97 (dd, 1H), 8.09 (s, 1H), 8.63 (d, 1H), 12.58 (br. s., 1H).

Example 13

2-(5-Chloro-9-ethyl-6-methyl-9H-carbazol-3-yl)-1-(2-methoxyethyl)-4-methyl-1H-benzimidazole-5-carboxylic Acid

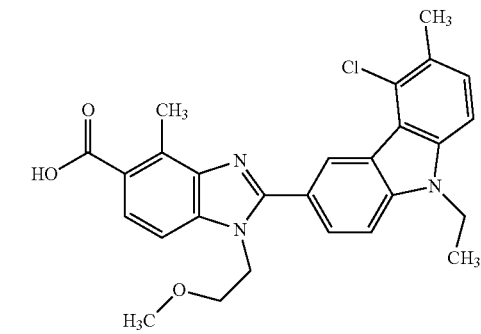 [SMILES: CCn1c2ccc(-c3nc4c(C)c(C(=O)O)ccc4n3CCOC)cc2c2c(Cl)c(C)ccc21]

Analogously to Example 1, 88 mg (0.37 mmol) of methyl 3-amino-4-[(2-methoxyethyl)amino]-2-methylbenzoate (Intermediate 8) and 100 mg (0.37 mmol) of 5-chloro-9-ethyl-6-methyl-9H-carbazole-3-carbaldehyde (Intermediate 7) gave initially methyl 2-(5-chloro-9-ethyl-6-methyl-9H-carbazol-3-yl)-1-(2-methoxyethyl)-4-methyl-1H-benzimidazole-5-carboxylate (111 mg, 61%), which was then converted further analogously to Example 2 into the title compound (95 mg, 94%).

$^1$H-NMR (300 MHz, DMSO-d6), δ [ppm]=1.35 (t, 3H), 2.54 (s, 3H), 2.89 (s, 3H), 3.15 (s, 3H), 3.75 (t, 2H), 4.46-4.60 (m, 4H), 7.48-7.57 (m, 2H), 7.61-7.67 (m, 1H), 7.81-7.87 (m, 2H), 7.99 (dd, 1H), 8.99 (d, 1H), COOH not stated.

Biological Examples

1. Syngeneic Mouse Endometriosis Model

Syngeneic induction of endometriosis in mice is a conventional animal model for testing the efficacy of substances for the therapy of endometriosis. Endometriosis is induced experimentally by transplantation of murine uterus fragments of a donor mouse of the same strain into the abdominal cavity of the recipient mouse. Female animals of the balb/c strain were used. The cycle of the mouse is determined by vaginal swab. Only donor animals in oestrus are used. The donor animals are sacrificed and the uterine horns are removed and then cut open longitudinally. Using a punch, 2 mm biopsies are punched out of the uteri, and these are subsequently sutured into the recipient animal. The recipient animals are anaesthetized and laparotomized. During the intervention, 6 punched-out uterus samples from a donor mouse are sutured to the parietal peritoneum of the recipient mouse. On the day after this intervention, a 4-week treatment with the substances to be tested is started. After 28 days, the animals are subjected to a final laparotomy and the dimensions of the lesions are determined. The adnate lesions are photographed and the area is measured using AxioVision software. 14 animals per treatment group are used.

2. Flow Cytometry

To obtain the cells from the peritoneum, 3 ml of cold PBS (phosphate buffered saline) are injected into the peritoneum of the dead animal and, after a gentle massage of the abdomen, removed again. The cells of this peritoneal lavage are spun down at 1400 rpm for 2 min and resuspended in 500 μl of PBS mit 2% FCS (fetal calf serum). For each stain with different antibody fluorochrome conjugate mixes, 100 μl of this cell suspension are used. To this end, the cells are spun down in 96-well plates, resuspended in 50 μl of an anitbody solution in anti-CD11 b-Pacific Blue (eBioscience) diluted 1:300, anti-F4/80-PE (eBioscience) diluted 1:200, anti-Gr1-APC-Cy7 (BD Pharmigen) diluted 1:200, anti-CD11c-PE-Cy7 (BD Pharmigen) diluted 1:400 and anti-MHCII-FITC (BD Pharmigen) diluted 1:400 and kept in the dark on ice for 20 min. 150 μl of PBS with 2% FCS are then added, and the cells are once more spun down at 1400 rpm for 2 min. The 200 μl of supernatant are discarded and the cells are washed with 200 μl of PBS with 2% FCS and spun down again. Subsequently, they are taken up in 200 μl of PBS with 2% FCS and 5 mg/ml DAPI (Sigma) diluted 1:5000, and the intensity of the fluorescence of the individual fluorochromes per cell is measured with a FACS Canto II flow cytometer.

3. Detection of the Antagonism of the Human Prostaglandin E2 (Subtype ER$_4$) Receptor Signal 3. 1 Detection Principle Detection of the Antagonization of the hEP4 Signal Binding of the agonist prostaglandin E2 (PGE2) to the EP4 subtype of the human hPGE2-R (hEP4-R) induces activation of membrane-bound adenylate cyclases and thus the formation of cAMP. In the presence of the phosphodiesterase inhibitor IBMX, this cAMP accumulates intracellularly and is, after cell lysis, employed in a competitive detection method. In this method, it competes with a fluorescently labelled cAMP (cAMP-d2) for binding to an anti-cAMP antibody labelled with an Eu cryptate. In the absence of cellular cAMP, a complex between the Eu-cryptate-labelled anti-cAMP antibody and the cAMP-d2 molecule is formed which, after excitation at 337 nm, allows a FRET-based (FRET=fluorescence resonance energy transfer) enery transfer to the cAMP-d2 tracer and results in a long-lasting fluorescence signal (emission at 665 and 620 nm). This signal is time-resolved, i.e. measured in a suitable measuring device once the background fluorescence has subsided (time resolved; TR-FRET). Additionally, well-ratio determination (emission 665 nm/emission 620 nm*10 000) allows variations in the individual measurements in the added amounts of detection reagents to be normalized.

Administration of prostglandin E2 and increase of intracellular cAMP reduces the FRET signal which increases again if the substance is antagonistically active.

3.2. Detection Method 3.2.1 Test for Antagonism (Figures Per Well of a 384-Well Plate):

4 μl of a suspension of hEP4-expressing cells (2500 cells/well) already comprising the cAMP-D2 tracer are added to the substance solutions (50 nl; 100% DMSO) initially charged in a test plate. After 20 minutes of pre-incubation at room temperature, 2 μl of a 3×PGE2 solution are added and the mixture is incubated in the presence of an EC80 concentration of the agonist (0.4 nM) for a further 60 min at room temperature (volume: ~6 μl), and the whole reaction is then stopped by addition of 2 μl of lysis buffer (volume: ~8 μl). After a further 20 min at room temperature, the cell lysate is measured in accordance with the instructions of the manufacturer in a measuring instrument suitable for TR-FRET (compare cAMP HTRF assay kit: Cisbio International 62AM6PEJ high range)

3.2.2 Test for Agonism (Figures Per Well of a 384-Well Plate):

4 μl of a suspension of hEP4-expressing cells (2500 cells/well) already comprising the cAMP-D2 tracer are added to the substance solutions (50 nl; 100% DMSO) initially charged in a test plate. After 20 minutes of pre-incubation at room temperature, 2 μl of cell medium are added and the mixture is incubated for a further 60 min at room temperature (volume: ~6 μl), and the whole reaction is then stopped by addition of 2 μl of lysis buffer (volume: ~8 μl). After a further 20 min at room temperature, the cell lysate is measured in accordance with the instructions of the manufacturer in a measuring instrument suitable for TR-FRET (cf. cAMP HTRF assay kit: Cisbio International 62AM6PEJ high range)

4. Detection of the Antagonism of the Human Prostaglandin E2 (Subtype EP2) Receptor Signal 4. 1 Detection Principle Binding of PGE2 to the EP2 subtype of the human PGE2 receptor induces activation of membrane-bound adenylate cyclases and leads to the formation of cAMP. In the presence of the phosphodiesterase inhibitor IBMX, the cAMP which has accumulated as a result of this stimulation and is released by cell lysis is employed in a competitive detection method. In this test, the cAMP present in the lysate competes with a fluorescently labelled cAMP (cAMP-d2) for binding to an anti-cAMP antibody labelled with an Eu cryptate.

The absence of cellular cAMP leads to a maximum signal owing to this cAMP-d2 molecule binding to the antibody. Excitation of the cAMP-d2 molecule at 337 nm leads to a fluorescence resonance energy transfer (FRET) to the Eu cryptate molecules of the anti-cAMP antibody (labelled therewith), followed by a long-lasting emission signal at 665 nm (and also at 620 nM). The two signals are measured in a suitable measuring device in a time-resolved manner, i.e. once the background fluorescence has subsided. Any increase of the low FRET signal owing to prostglandin E2 administration (measured as change in the well ratio=emission$_{665nm}$/emission$_{620nm}$*10 000) indicates the action of antagonists.

4.2. Detection Method 4.2.1. Test for Antagonism (Figures Per Well of a 384-Well Plate):

4 µl of a cAMP-d2/cell suspension (625 000 cells/ml) were added to a test plate with the substance solutions (0.05 µl; 100% DMSO, concentration range 0.8 nM-16.5 µM) already charged. After 20 minutes of pre-incubation at room temperature, 2 µl of a 3×PGE2 solution (1.5 nM, in PBS-IBMX) were added and the mixture was incubated in the presence of the agonist for a further 60 min at room temperature (volume: ~6 µl). The reaction was then stopped by addition of 2 µl of lysis buffer and the mixture was incubated at room temperature for a further 20 min prior to the actual measurement (volume: ~8 µl).

5. Detection of the Antagonism of the Human Prostaglandin D Receptor Signal 5.1 Detection Principle Binding of prostaglandin D2 to the human PGD receptor induces activation of membrane-bound adenylate cyclases and leads to the formation of cAMP. In the presence of the phosphodiesterase inhibitor IBMX, the cAMP which has accumulated as a result of this stimulation and is released by cell lysis is employed in a competitive detection method. In this test, the cAMP present in the lysate competes with a fluorescently labelled cAMP (cAMP-d2) for binding to an anti-cAMP antibody labelled with an Eu cryptate.

The absence of cellular cAMP leads to a maximum signal owing to this cAMP-d2 molecule binding to the antibody. Excitation of the cAMP-d2 molecule at 337 nm leads to a fluorescence resonance energy transfer (FRET) to the Eu cryptate molecules of the anti-cAMP antibody (labelled therewith), followed by a long-lasting emission signal at 665 nm (and also at 620 nM). The two signals are measured in a suitable measuring device in a time-resolved manner, i.e. once the background fluorescence has subsided. Any increase of the low FRET signal owing to prostglandin E2 administration (measured as change in the well ratio=emission$_{665nm}$/emission$_{620nm}$*10 000) indicates the action of antagonists.

5.2. Detection Method 5.2.1. Test for Antagonism (Figures Per Well of a 384-Well Plate):

4 µl of a cAMP-d2/cell suspension (625 000 cells/ml) were added to a test plate with the substance solutions (0.05 µl; 100% DMSO, concentration range 0.8 nM-16.5 µM) already charged. After 20 minutes of pre-incubation at room temperature (RT), 2 µl of a 3×PGD2 solution (6 nM, in PBS-IBMX) were added and the mixture was incubated in the presence of the agonist for a further 30 min at RT (volume: ~6 µl). The reaction was then stopped by addition of 2 µl of lysis buffer and the mixture was incubated at RT for a further 20 min prior to the actual measurement (volume: ~8 µl).

TABLE 1

Antagonization of the activity of the human EP4 receptor by the compounds according to the invention

| Example | hEP4 antagonization IC$_{50}$ [M] |
|---|---|
| 1 | 3.2E−8 |
| 2 | 1.1E−8 |
| 3 | 4.0E−8 |

TABLE 1-continued

Antagonization of the activity of the human EP4 receptor by the compounds according to the invention

| Example | hEP4 antagonization IC$_{50}$ [M] |
|---|---|
| 4 | 2.4E−9 |
| 6 | 2.0E−9 |
| 7 | 2.4E−9 |
| 8 | 1.9E−9 |
| 9 | 6.2E−8 |
| 10 | 1.5E−9 |
| 11 | 4.7E−8 |
| 12 | 2.8E−9 |
| 13 | 2.3E−8 |

REFERENCES

Giudice L C; Endometriosis; N Engl J Med 2010; 362:2389-98.

Chishima F, Hayakawa S, Sugita K, Kinukawa N, Aleemuzzaman S, Nemoto N, Yamamoto T, Honda M: Increased expression of cyclooxygenase-2 in local lesions of endometriosis patients. Am J Reprod. Immunol 2002; 48:50-56.

Sales K J and Jabbour H N; Cyclooxygenase enzymes and prostaglandins in pathology of the endometrium. Reproduction (2003) 126, 559-567.

Stratton P and Berkley K J; Chronic pelvic pain and endometriosis: translational evidence of the relationship and implications; Human Reproduction Update, Vol. 0, No. 0 pp. 1-21, 2010.

Petraglia F, Hornung D, Seitz C, Faustmann T, Gerlinger C, Luisi S, Lazzeri L, Strowitzki T; Reduced pelvic pain in women with endometriosis: efficacy of long-term dienogest treatment; Arch Gynecol Obstet, 2012 January; 285(1):167-73.

The invention claimed is:

1. A compound of the general formula (I)

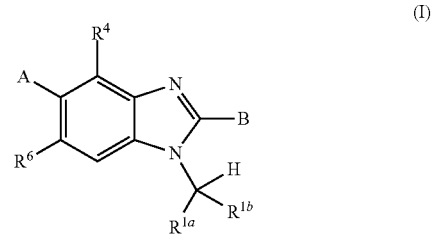

in which

A represents $R^{11}O-C(=O)-(CH_2)_p-$,

B represents a group

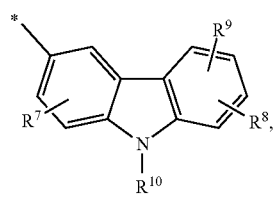

where * denotes the point of attachment in the molecule,
$R^{1a}$ represents hydrogen,
$R^b$ represents methoxymethyl,
$R^4$ represents hydrogen, fluorine or methyl,
$R^6$ represents hydrogen,
$R^7$ represents hydrogen,
$R^8$ represents fluorine, chlorine or methyl,
$R^9$ represents fluorine, chlorine, bromine or methyl, or
$R^9$ represents bromine and simultaneously $R^8$ represents hydrogen,
$R^{10}$ represents ethyl,
$R^{11}$ represents hydrogen, methyl or ethyl,
m is 0, 1, 2 or 3,
n is 0, 1, 2 or 3,
p is 0,
q is 1, 2 or 3 and
r is 0, 1, 2 or 3,
and a diastereomer, enantiomer, solvate and salt or cyclodextrin clathrate thereof.

2. A compound selected from a group consisting of the following compounds:
methyl 2-(6-bromo-9-ethyl-9H-carbazol-3-yl)-1-(2-methoxyethyl)-4-methyl-1H-benzimidazole-5-carboxylate;
2-(6-bromo-9-ethyl-9H-carbazol-3-yl)-1-(2-methoxyethyl)-4-methyl-1H-benzimidazole-5-carboxylic acid;
methyl 2-(9-ethyl-8-fluoro-6-methyl-9H-carbazol-3-yl)-1-(2-methoxyethyl)-4-methyl-1H-benzimidazole-5-carboxylate;
2-(9-ethyl-8-fluoro-6-methyl-9H-carbazol-3-yl)-1-(2-methoxyethyl)-4-methyl-1H-benzimidazole-5-carboxylic acid;
methyl 2-(9-ethyl-6-fluoro-8-methyl-9H-carbazol-3-yl)-1-(2-methoxyethyl)-4-methyl-1H-benzimidazole-5-carboxylate;
2-(9-ethyl-6-fluoro-8-methyl-9H-carbazol-3-yl)-1-(2-methoxyethyl)-4-methyl-1H-benzimidazole-5-carboxylic acid;
2-(9-ethyl-6-fluoro-8-methyl-9H-carbazol-3-yl)-4-fluoro-1-(2-methoxyethyl)-1H-benzimidazole-5-carboxylic acid;
2-(9-ethyl-8-fluoro-6-methyl-9H-carbazol-3-yl)-4-fluoro-1-(2-methoxyethyl)-1H-benzimidazole-5-carboxylic acid;
ethyl 2-(9-ethyl-8-fluoro-6-methyl-9H-carbazol-3-yl)-1-(2-methoxyethyl)-1H-benzimidazole-5-carboxylate;
2-(9-ethyl-8-fluoro-6-methyl-9H-carbazol-3-yl)-1-(2-methoxyethyl)-1H-benzimidazole-5-carboxylic acid;
methyl 2-(8-chloro-9-ethyl-6-methyl-9H-carbazol-3-yl)-1-(2-methoxyethyl)-4-methyl-1H-benzimidazole-5-carboxylate;
2-(8-chloro-9-ethyl-6-methyl-9H-carbazol-3-yl)-1-(2-methoxyethyl)-4-methyl-1H-benzimidazole-5-carboxylic acid;
2-(5-chloro-9-ethyl-6-methyl-9H-carbazol-3-yl)-1-(2-methoxyethyl)-4-methyl-1H-benzimidazole-5-carboxylic acid; and
a diastereomer, enantiomers, solvate and salt or cyclodextrin clathrates thereof.

3. A pharmaceutical composition comprising a compound according to claim 1.

4. The pharmaceutical composition of claim 3, further comprising an inert, nontoxic, pharmaceutically suitable auxiliary.

5. The pharmaceutical composition of claim 3, wherein said composition is for enteral, parenteral, vaginal, intrauterine and oral administration.

6. The compound of claim 1, wherein $R^8$ is methyl and $R^9$ is fluorine, chlorine or bromine.

7. The compound of claim 1, wherein $R^8$ is fluorine or chlorine and $R^9$ is methyl.

8. A compound of the general formula (I)

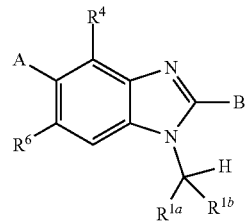

(I)

in which
A represents $R^{11}O—C(=O)—(CH_2)_p—$,
B represents a group

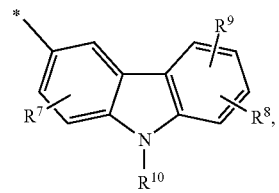

where * denotes the point of attachment in the molecule,
$R^{1a}$ represents hydrogen,
$R^{1b}$ represents methoxymethyl,
$R^4$ represents hydrogen, fluorine or methyl,
$R^6$ represents hydrogen,
$R^7$ represents hydrogen,
$R^8$ represents fluorine, chlorine or methyl,
$R^9$ represents fluorine, chlorine, bromine or methyl,
$R^{10}$ represents ethyl,
$R^{11}$ represents hydrogen, methyl or ethyl,
m is 0, 1, 2 or 3,
n is 0, 1, 2 or 3,
p is 0,
q is 1, 2 or 3 and
r is 0, 1, 2 or 3,
and a diastereomer, enantiomer, solvate and salt or cyclodextrin clathrate thereof.

9. A composition comprising a compound of claim 2 and an inert, nontoxic pharmaceutically suitable auxiliary.

* * * * *